(12) United States Patent
Vazifehdan et al.

(10) Patent No.: US 11,478,284 B2
(45) Date of Patent: Oct. 25, 2022

(54) SURGICAL REPOSITIONING INSTRUMENT

(71) Applicant: Premiere Medical GmbH, Erbach (DE)

(72) Inventors: Farzam Vazifehdan, Stuttgart (DE); Mathias Pippan, Mainz (DE); Michael Reith, Mainz (DE); C. Michael Nilsson, Moreland Hills, OH (US); Helmut Schönhöffer, Erbach (DE)

(73) Assignee: Premiere Medical GmbH, Erbach (DE)

( * ) Notice: Subject to any disclaimer, the term of this patent is extended or adjusted under 35 U.S.C. 154(b) by 505 days.

(21) Appl. No.: 16/426,271

(22) Filed: May 30, 2019

(65) Prior Publication Data

US 2019/0274741 A1    Sep. 12, 2019

Related U.S. Application Data

(63) Continuation of application No. PCT/EP2017/080680, filed on Nov. 28, 2017.

(30) Foreign Application Priority Data

Dec. 8, 2016    (DE) ...................... 10 2016 224 503.1

(51) Int. Cl.
  *A61B 17/70*    (2006.01)
(52) U.S. Cl.
  CPC ...... *A61B 17/7086* (2013.01); *A61B 17/7037* (2013.01)
(58) Field of Classification Search
  CPC ............. A61B 17/7086; A61B 17/708; A61B 17/7083; A61B 17/7085; A61B 17/7088; A61B 17/7089; A61B 17/7091; A61B 17/7077; A61B 17/7079
  See application file for complete search history.

(56) References Cited

U.S. PATENT DOCUMENTS 7,909,835 B2 *  3/2011  Oribe ................. A61B 17/7086
                                                606/104
8,377,104 B2 *  2/2013  Jones ................. A61B 17/7091
                                                606/279

(Continued)

FOREIGN PATENT DOCUMENTS

EP         2 249 723 B1    6/2014

*Primary Examiner* — Jan Christopher L Merene
(74) *Attorney, Agent, or Firm* — Hackler Daghighian Martino & Novak

(57) ABSTRACT

A surgical repositioning instrument for lowering and fixing a fixing rod in the tulip head of a bone screw has a coupling sleeve with two distal latching arms. A locking sleeve is longitudinally displaceable on the coupling sleeve between a release and locking position. A rod presser contacts and lowers the fixing rod, which is arranged displaceably within the coupling sleeve. Arranged in a through bore in the handle part is the locking sleeve, coupling sleeve and rod presser. On a grip part, an actuating lever is pivotally mounted to advance the rod presser relative to the coupling sleeve. The actuating lever has a laterally projecting force arm and a load arm which is coupled to the rod presser. The locking sleeve protrudes in its release position and is independently slid into its locking position by the rod presser acting on its proximal end with an axially directed force.

21 Claims, 20 Drawing Sheets

(56) References Cited

U.S. PATENT DOCUMENTS

| | | |
|---|---|---|
| 2006/0089651 A1* | 4/2006 | Trudeau .............. A61B 17/7086 606/86 R |
| 2007/0213722 A1* | 9/2007 | Jones ................. A61B 17/7091 606/86 A |
| 2009/0228053 A1 | 9/2009 | Kolb et al. |
| 2010/0324609 A1 | 12/2010 | Jones et al. |
| 2011/0202096 A1 | 8/2011 | White et al. |
| 2012/0191144 A1 | 7/2012 | Peultier et al. |
| 2012/0215266 A1 | 8/2012 | Jones |
| 2012/0283786 A1 | 11/2012 | Rezach et al. |

* cited by examiner

SURGICAL REPOSITIONING INSTRUMENT

CROSS-REFERENCE TO RELATED APPLICATIONS

This continuation application claims priority to PCT/EP2017/080680 filed on Nov. 28, 2017 which has published as WO 2018/104112 A1 and also the German application number 10 2016 224 503.1 filed on Dec. 8, 2016, the entire contents of which are fully incorporated herein with these references.

DESCRIPTION

Field of the Invention

The invention relates to a surgical repositioning instrument for lowering and fixing a fixing rod in the tulip head of a bone screw.

BACKGROUND OF THE INVENTION

In spinal instrumentation, implant systems with bone screws are used in clinical practice, which are connected to each other via fixing rods, which are usually resistant to bending and torsion. The bone screws of these so-called rod screw systems have a threaded shaft with a so-called tulip head, which has a fixing rod connector. For lowering and fixing the fixing rod in the fixing rod connector of such tulip head, so-called repositioning instruments are used. The repositioning instruments available on the market are often difficult to handle, so that, in particular with minimally invasive surgical access routes, unnecessary tissue trauma can sometimes not be avoided. The healing process can thereby be delayed. In addition, proper hygienic treatment, i.e. cleaning and disinfection or sterilization, of the repositioning instruments available on the market is often only possible with a great deal of time and expense.

It is therefore an object of the invention to provide a repositioning instrument that has a simplified and at the same time safe handling and preferably a simplified hygienic treatment.

SUMMARY OF THE INVENTION

The repositioning instrument according to the invention has the features specified in the independent claim. Further embodiments of the invention are specified in the dependent claims and in the description.

The surgical repositioning instrument is characterized by a particularly simple structural design and simplified handling. With its at least two latching arms of the coupling sleeve, the repositioning instrument can be slipped in a tissue-conserving manner onto the tulip head of a respective bone screw, which was previously anchored in the bone tissue of the patient, in the direction of the longitudinal axis of the repositioning instrument and latched to the tulip head. The latching arms are deflected or steered only so far radially outward only by their contact with the tulip head relative to the longitudinal axis of the repositioning instrument so far that the tulip head can slide and lock with them in the axial direction between the at least two latching arms. The tulip head is arranged for a simplified approach and coupling of the repositioning instrument to the surgical site, a guide rod can additionally be inserted, which is inserted into the tulip housing and coupled thereto, preferably in a tensile-resistant, releasable manner. This can be achieved, for example, by screwing the guide rod into the usually present internal thread of the wall legs of the tulip head or else by clamping or latching the guide rod in the tulip head.

The repositioning instrument can then be threaded onto the guide rod with the sleeve-shaped rod presser and advanced in the axial direction along the guide rod to the tulip head. The locking sleeve of the repositioning instrument can be moved from its release position to its locking position by the user (surgeon) of the repositioning instrument in a simple and convenient manner, regardless of the rod presser or its operation—thus without a so-called repositioning, i.e. lowering, of the fixing rod by means of the rod presser. In the locking position, the locking sleeve engages over the latching arms of the coupling sleeve on the outside in a radial direction, so that it is secured in its coupling or latched position on the tulip housing of the bone screw.

In the repositioning instrument according to the invention, the locking sleeve and the rod presser are thus mechanically decoupled from each other. The two components are in other words not able to be mechanically displaced together in a motion-coupled manner. This considerably simplifies the handling and controllability of the repositioning instrument. In addition, unwanted movements of the repositioning instrument in the surgical site can be further reduced. Overall, the risk of tissue trauma can again be further reduced. In addition, this can improve the operating safety of the repositioning instrument. Also, the structural design of the repositioning instrument can be kept simple, which offers advantages for the manufacture, maintenance and hygienic treatment of the repositioning instrument.

The handle part allows a comfortable and secure holding of the repositioning instrument and is preferably tuned in its shape to the anatomy of the human hand. The actuating lever pivotally mounted on the handle part serves to advance the rod presser relative to the coupling sleeve, i.e. the (complete) lowering of the fixing rod into the tulip head of the bone screw. The actuating lever is preferably pivotable about a pivot axis arranged orthogonally to the longitudinal axis. As a result, the operating lever can be conveniently operated with the fingers of the user's hand holding the repositioning instrument. Of course, the power arm is chosen to be functionally longer than the load arm, in order to ensure a strength-saving handling and thus a superior control of the repositioning instrument. The rod presser is preferably designed as a hollow profile, so that the above-mentioned fixing rod can be fixed in the tulip head of the bone screw by means of a fixing screw and a rotary tool inserted into the rod presser.

An even higher degree of operating safety of the repositioning instrument can be achieved according to the invention in that the locking sleeve can be locked in its locking position relative to the coupling sleeve, in particular latched to the handle part. Unintentional release of the latching arms of the locking sleeve can be reliably prevented.

According to a particularly preferred development of the invention, the load arm of the actuating lever is coupled with the rod presser via a carrier slide that is longitudinally displaceable in the handle part. In this case, the load arm thus engages on the carrier slide on the rod presser. By using such a carrier slide, the pivoting movement of the actuating handle can be implemented in a translational movement of the rod presser relative to the coupling sleeve in a manner which is structurally simple and less susceptible to interference. In addition, the handle part of the repositioning instrument can be made compact and at the same time act as a protective housing for the carrier slide.

The carrier slide is preferably made of metal with regard to its load-carrying capacity. For mechanically connecting the carrier slide with the actuating lever, the carrier slide can have bearing journals which engage in each case in a slot of the actuating lever, especially of the load arm. The bearing journals may extend outwardly through axially extending (guide) slots of the handle part. This allows for a particularly precise and low-interference guidance of the carrier slide to be achieved.

According to the invention, the handle part preferably has a side wall element with a, preferably T-shaped, guide or longitudinal groove in which the carrier slide is guided. Through this groove guide, a malfunction of the carrier slide, for example, by its tilting in the handle part, can be counteracted. Also, the side wall element can be provided inexpensively as an attachment of the handle part with low manufacturing tolerances, i.e. as a precision component. In the case of the T-shaped groove, a particularly reliable multi-point or multi-line guidance of the carrier slide can be realized.

The side wall element according to the invention can be pivotally mounted on the handle part. As a result, on the one hand, the functional state of the repositioning instrument in the area of the carrier slide can be checked visually. If the carrier slide is guided or displaceably mounted in a T-shaped guide groove of the side wall element, then the side wall element can have a dual function. Thus, the carrier slide can be brought out of engagement with the presser rod by pressing out the side wall element out of the grip part of the carrier slide. This allows a rapid disassembly of the repositioning instrument for its hygienic treatment, i.e. cleaning or disinfection.

According to an alternative development of the invention, the rod presser is provided with one or more lateral profile extensions which extends/extend away from the rod presser in a radial direction on the outside. These profile extensions can be directly coupled with the load arm of the actuating lever.

According to a development of the invention, the locking sleeve and the coupling sleeve each have a lateral wall opening, which are arranged in the radial direction at least partially aligned with each other in the ready state of the repositioning instrument, wherein the carrier slide extends through the two wall openings of these sleeves in the radial direction. As a result, the repositioning instrument can be made particularly compact and with a small number of required parts.

With regard to a further improved handling of repositioning instrument, the actuating lever is preferably deflected from its rest position or moved out against the force of a spring element, in particular a torsion spring element.

For a simple assembly and disassembly of the repositioning instrument, the coupling sleeve may have two, preferably resiliently articulated, radial projections which extend in the operational state of the repositioning instrument each in the radial direction through a slot-shaped recess of the locking sleeve into a bearing recess of the handle part. As a result, a (releasable) non-rotatable locking of the locking sleeve as well as of the coupling sleeve on the handle can be achieved in a simple and cost-effective manner. In addition, the coupling sleeve can be fixed on the handle part in the axial direction (releasably). The radial projections are preferably integrally formed on spring arms of the locking sleeve, which are formed as one piece with the locking sleeve. This offers advantages in the manufacture, assembly and preparation of the repositioning instrument.

The handle part may, according to the invention, have at one end an openable bearing bracket, which preferably consists of metal. The bearing bracket may comprise or form the bearing recesses for the radial projections of the coupling sleeve. If the bearing bracket is made of metal, then a high mechanical load-bearing capacity of the handle part, in particular in the region of its head section, can be ensured. In addition, by means of such a bearing bracket, unintentional removal of the locking sleeve as well as the coupling sleeve from the handle part in the axial direction can be prevented.

The rod presser can be latched or locked, according to the invention, preferably by means of a latching device in at least one axial displacement position, preferably in different axial (feed) positions, relative to the coupling sleeve. In the former case, the rod presser is preferably axially fixed in position in its distal lowered position relative to the coupling sleeve. In the latter case, the rod presser can be secured to variable axial displacement positions relative to the coupling sleeve or the tulip housing. This allows a particularly energy-saving and careful operation of the repositioning instrument. After completely lowering the fixing rod in the tulip housing of the bone screw, the repositioning instrument can be released by the user so that the fixing rod can be fixed permanently in the tulip head, for example by means of a screw to be screwed into the tulip head, without having to hold the repositioning instrument.

The latching device comprises, according to a particularly preferred embodiment, a latching element which is in the handle part, preferably displaceably mounted, and which cooperates with a latching profile of the rod presser. From a design point of view, it has proven to be particularly advantageous if the latching element annularly surrounds the locking sleeve, the coupling sleeve and the rod presser in the operational state of the repositioning instrument. As a result, the latching element can be arranged captive on one side in the handle part. On the other hand, a particularly large-scale axial contact of the latching element can be realized on the rod presser. This provides a high load capacity of the latching connection between the handle part and the rod presser.

For a particularly simple and safe use and at the same time an operational use of the repositioning instrument that is not very susceptible to faults, the latching element is preferably arranged radially by the force of a spring element in the direction of its detent position on the rod presser. As a result, a self-latching function of the latching device can be achieved. Also, this can be reliably counteracted by a user-side operating error of the repositioning instrument.

According to a particularly preferred embodiment of the invention, the locking sleeve can be locked by means of the latching element in the axial direction in its locking position relative to the coupling sleeve. The latching element thus has a dual function in this case, whereby the number of required components of the repositioning instrument can be further minimized. This offers advantages in the manufacture, assembly and maintenance as well as in the hygienic preparation of the instrument.

Particularly preferably, the latching element in the locking position of the locking sleeve extends in sections over the above-explained wall opening of the locking sleeve in the radial direction in the locking sleeve and abuts a lower edge of the wall opening of the locking element in the axial direction. As a result, unintentional axial (rear) displacement of the locking sleeve from its (once reached) locking position can be reliably avoided. It is understood that the latching element in this regard must be stored without or with only a slight axial play in the handle part. For storage of the latching element, the handle part may in particular have a laterally open receiving compartment. In other words, the receiving compartment has a sidewall opening.

The coupling sleeve may have at its distal free end portion a guide arm for the tulip head, which extends in the axial direction between the two latching arms and is spaced from each of these forming an axial gap. The guide arm is preferably formed rigidly compared to the latching arms, i.e. dimensionally stable in the radial direction. As a result, the repositioning instrument can once again be attached more simply to the tulip head of the bone screw and secured even more reliably against it avoiding undesired slippage from the tulip head. The two latching arms and the guide arm preferably extend over half or almost half of the total circumference of the coupling sleeve.

The coupling sleeve may, according to a preferred embodiment of the invention, comprise two further latching arms, between which a further guide arm preferably extends in the axial direction. As a result, the tulip head can be grasped on the circumference at further positions, whereby a coupling of the repositioning instrument with the tulip head of the bone screw can be achieved which can be subjected to a particularly high degree of mechanical stress.

The locking sleeve preferably has guide tongues at its distal free end section, which in each case engage in a corresponding longitudinal groove of the coupling sleeve, wherein the longitudinal grooves are arranged at least in sections on a side flank of one of the latching arms. As a result, the latching arms of the coupling sleeve can be better secured again by the arranged locking sleeve in its locking position avoiding undesired lateral slippage from the tulip head.

The longitudinal grooves of the coupling sleeve can each extend to the proximal end of the coupling sleeve according to the invention. As a result, the locking sleeve can be mounted in a simplified manner on the coupling sleeve and the two components can at the same time be connected to one another in a rotationally fixed manner. This enables a particularly reliable function of the repositioning instrument as well as a high degree of operating safety.

According to a preferred embodiment of the invention, the locking sleeve can be displaceable in the locking position from its release position against the force of a spring element which is preferably arranged within the locking sleeve. After unlocking the above-mentioned latching element, the locking sleeve can thereby slide back automatically (by spring force) on the coupling sleeve in its initial position or in its rest position.

With regard to the smallest possible mass of the repositioning instrument, the handle part may have a main body which consists of plastic or a plastic composite material. Load-bearing parts of the repositioning instrument may consist of a metal. In that regard, in particular, the head or the foot portion of the handle part may partially or completely be made of metal.

It is understood that the repositioning instrument preferably consists entirely of autoclavable materials.

BRIEF DESCRIPTION OF THE DRAWINGS

Further advantages of the invention will become apparent from the description and the drawings. The embodiments shown and described are not to be understood as exhaustive enumeration, but rather have exemplary character for the description of the invention.

In the drawings.

DETAILED DESCRIPTION OF THE PREFERRED EMBODIMENTS

Figure 1:
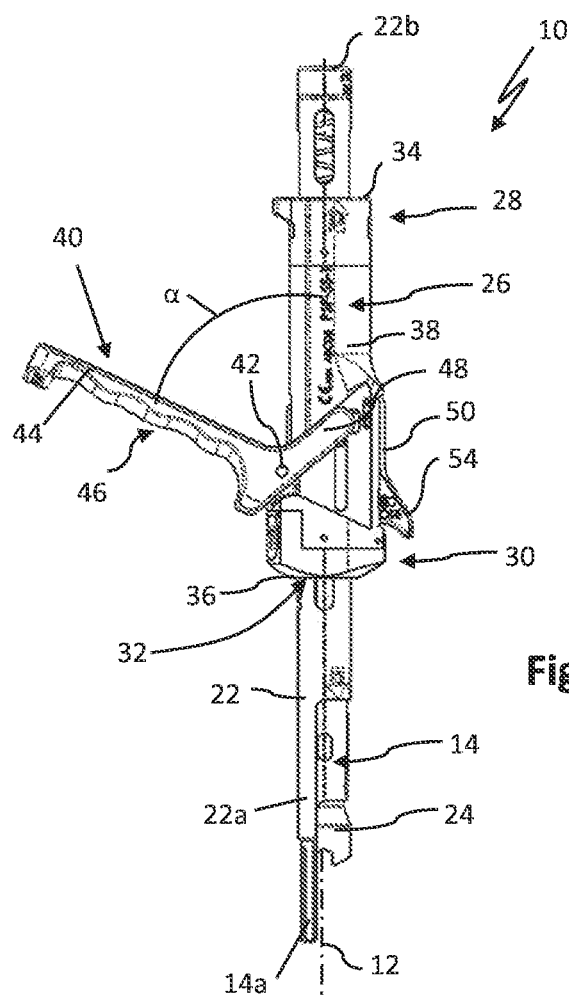
FIG. 1 shows a repositioning instrument for lowering and fixing a fixing rod in the tulip head of a bone screw, having a handle part and a plurality of sleeves which are coaxially arranged to the longitudinal axis and extend into the handle part, in a first perspective view.
Figure 2:
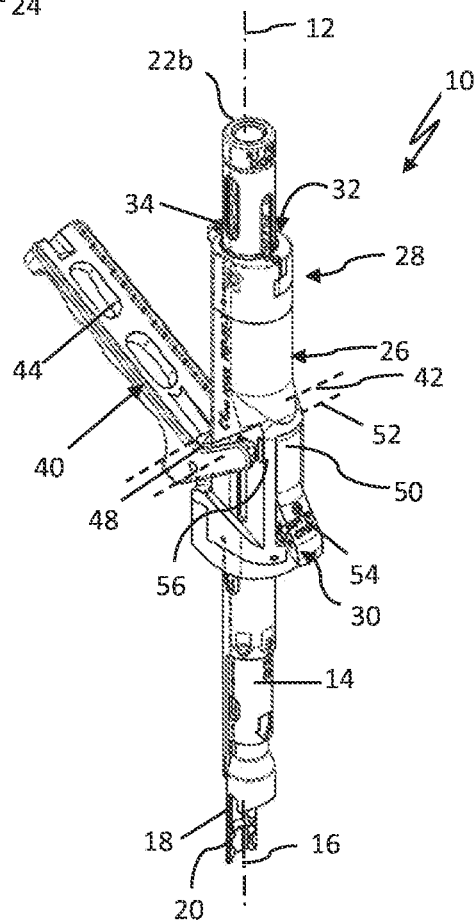
FIG. 2 shows the repositioning instrument according to FIG. 1 in another perspective view.
Figure 3:
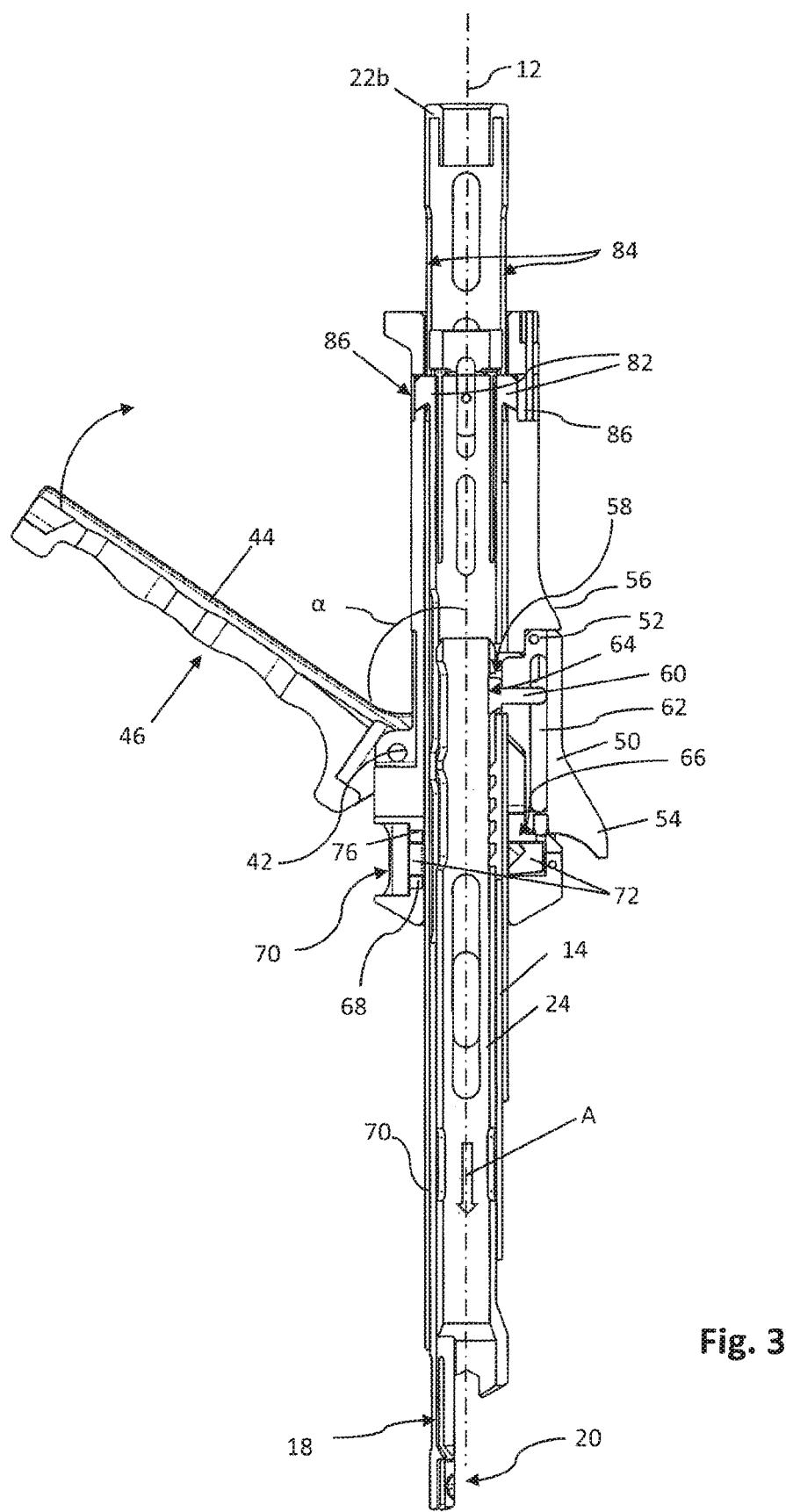
FIG. 3 shows the repositioning instrument according to FIG. 1 in a longitudinal section.

In FIGS. 1 and 3, a surgical repositioning instrument for spinal surgery, generally designated 10, is shown in a perspective view. The repositioning instrument 10 serves to lower a so-called fixing rod in the tulip head of a bone screw (not shown in FIGS. 1 to 3) and to fix it in the tulip head by means of a screw or the like. Such repositioning instruments 10 are also referred to as so-called "persuaders".

The repositioning instrument 10 is shown in FIGS. 1 to 2 in its operative operating state. The repositioning instrument 10 comprises a longitudinal axis 12 and three components which are at least partially sleeve-shaped and which are arranged coaxially on the longitudinal axis of the repositioning instrument 10.

A coupling sleeve 14 is used for coupling the repositioning instrument 10 on the tulip head of the bone screw. The coupling sleeve 14 has a longitudinal axis 16 which coincides with the longitudinal axis 12 of the repositioning instrument 10. The coupling sleeve 14 has a distal end portion 14a with two latching arms 18. The latching arms 18 are resiliently deflectable in a direction radial to the longitudinal axis 16 of the coupling sleeve 14 and to the longitudinal axis 12 of the repositioning instrument, so that the repositioning instrument 10 can be plugged over the latching arms 18 on the tulip housing of the bone screw and locked with this. A free (distal) end portion of the latching arms 18 is designated 20.

A blocking or locking sleeve 22 is arranged on the coupling sleeve 14, which is arranged longitudinally displaceable between a proximal release position shown in FIGS. 1 to 3 and a distal locking position. By the locking sleeve 22 arranged in the release position, the radial deflection of the latching arms 18 of the locking sleeve is allowed, while such is inhibited or blocked when the locking sleeve 22 is arranged in the locking position.

A pressure member or rod presser 24 is used for contacting and lowering of the fixing rod. The rod presser 24 is arranged to be displaceable within the coupling sleeve between a (proximal) rest or initial position and a (distal) lowering position relative to the coupling sleeve 14 in the axial direction.

The repositioning instrument 10 furthermore has a handle part 26 with a head section 28 and a foot section 30. The handle part 26 is provided with a longitudinal axial through bore 32. The through bore 32 extends here from the head portion 28 to the foot portion 30 and from the proximal end 34 of the handle part 26 to the distal end 36 of the handle portion 26. The radially outer locking sleeve 22, the radially inwardly disposed rod presser 24 and also the coupling sleeve 14 arranged between the locking sleeve 22 and the rod presser 24 extend into the through bore 32. The locking sleeve 22 protrudes with its proximal end 22b in the axial direction over the handle part 26. In other words, the locking sleeve 22 projects beyond the handle part 26 in the proximal direction.

Here, the handle part 26 comprises a main body 38 which, for reasons of weight, preferably consists of plastic or a plastic composite material. On the handle part 26 or on the main body 38, an actuating lever 40 for the rod presser is mounted around a first pivot axis 42. The first pivot axis is aligned orthogonally to the longitudinal axis 12. The actuation lever 40 has a force arm 44 with a preferably ergonomically shaped finger receptacle 46 for the user of the repositioning instrument. The force arm 44 can be moved manually from its neutral position shown in FIG. 1, in which the force arm 44 extends away from the handle part 26 to the side at an acute angle α to the longitudinal axis 12 of the repositioning instrument 10, around the first pivot axis 42, to the handle part 26, in order to move or lower the rod presser 24 in the axial direction relative to the coupling sleeve 14. The actuating lever 40 further has a fork-shaped load arm 48, which is preferably integrally connected to the force arm 44. The force arm 44 is coupled for movement with the rod presser 24, as explained in more detail below. The load arm 48 of the actuating lever 40 may have material recesses for weight reasons.

The handle part 26 also has a flap-like side wall element 50, which is mounted on the main body 38 of the handle part 26 around a second pivot axis 52. The second pivot axis 52 is arranged orthogonally to the longitudinal axis 12 of the repositioning instrument 10. The side wall element 50 has an actuating extension 54. If the side wall element 50 is arranged in its closed position shown in FIGS. 1 to 3, i.e. if the repositioning instrument 10 is in the ready state, the actuating extension 54 protrudes beyond the outside 56 of the handle part 26 in the radial direction. The side wall element 50 can be pivoted out of the housing part 26 out of the closed position in order to unlock the repositioning instrument 10 and disassemble it after use for cleaning or maintenance purposes.

Figure 4:
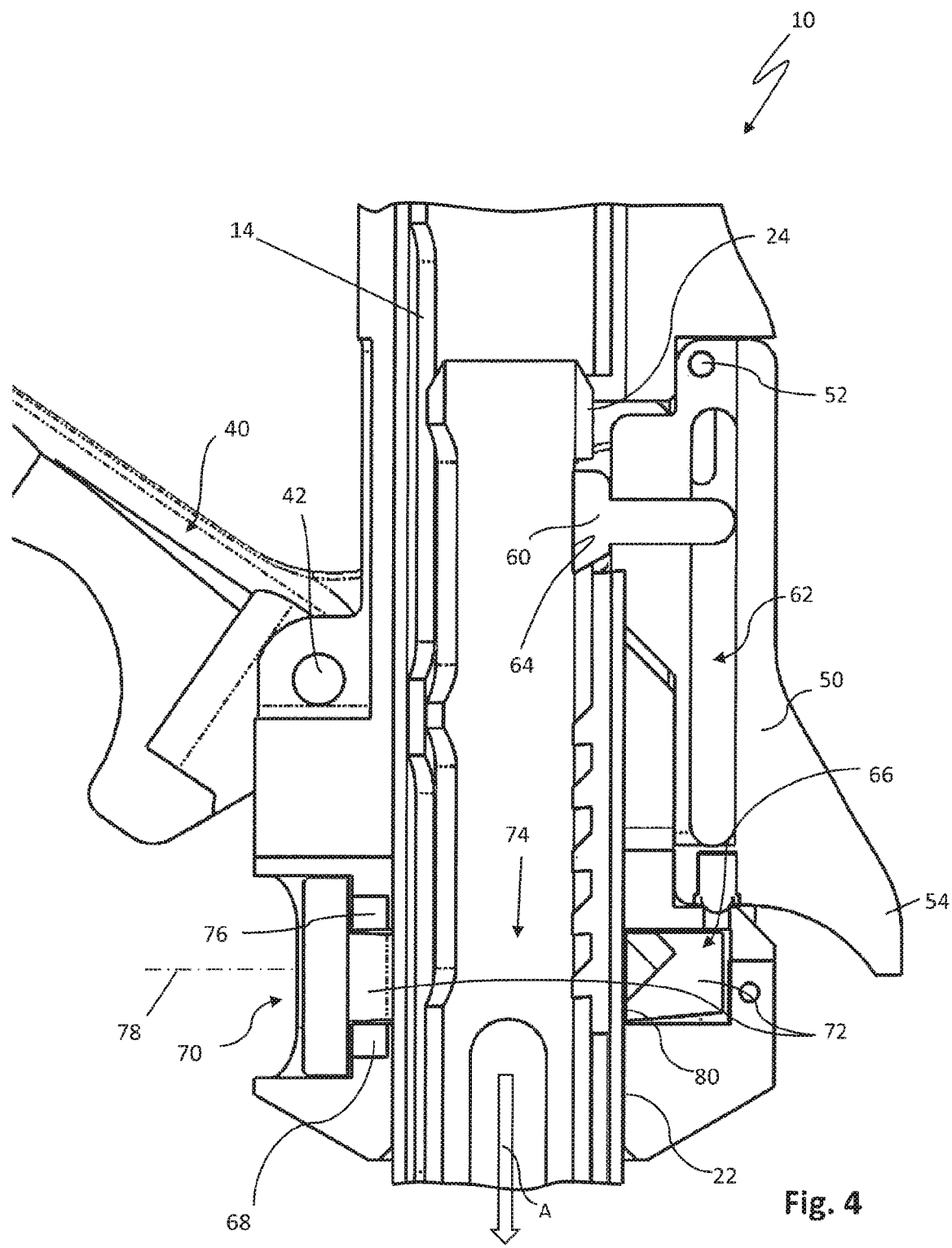
FIG. 4 shows an enlarged detail view of the repositioning instrument according to FIG. 3.
Figure 7:
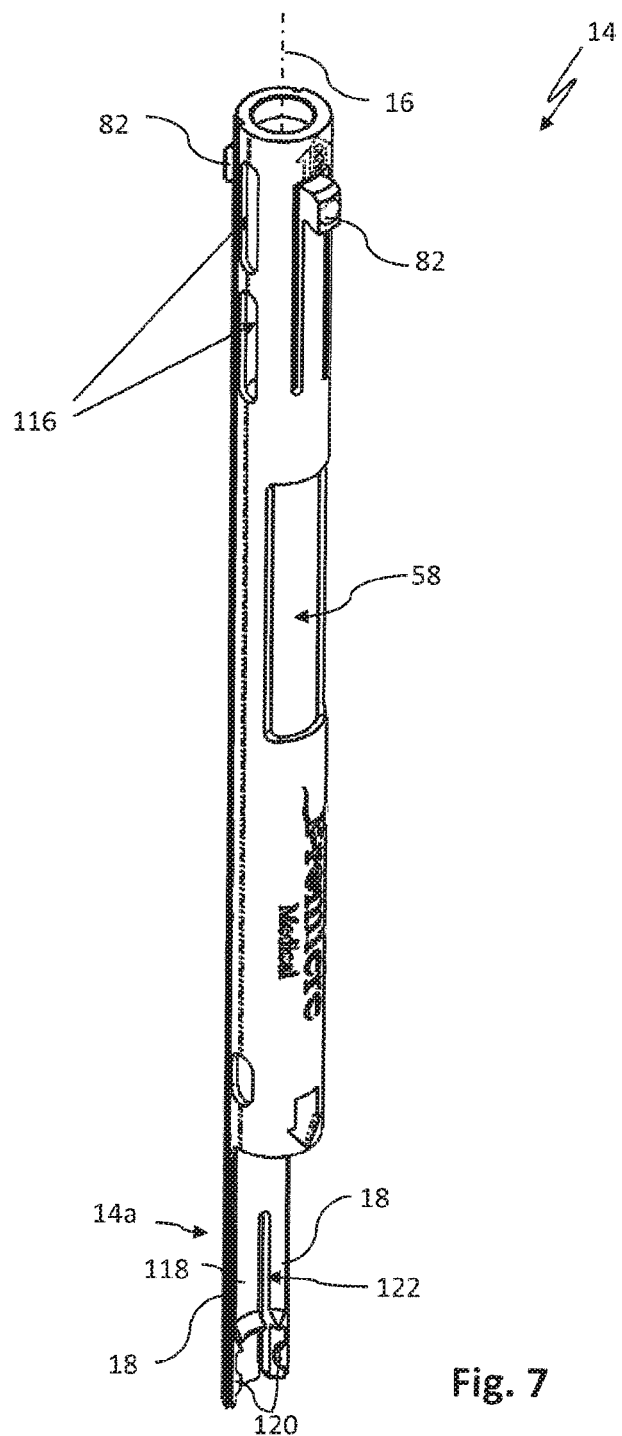
FIG. 7 shows a coupling sleeve of the repositioning instrument according to FIG. 1 with two distal latching arms, in a cut away perspective view.
Figure 8:
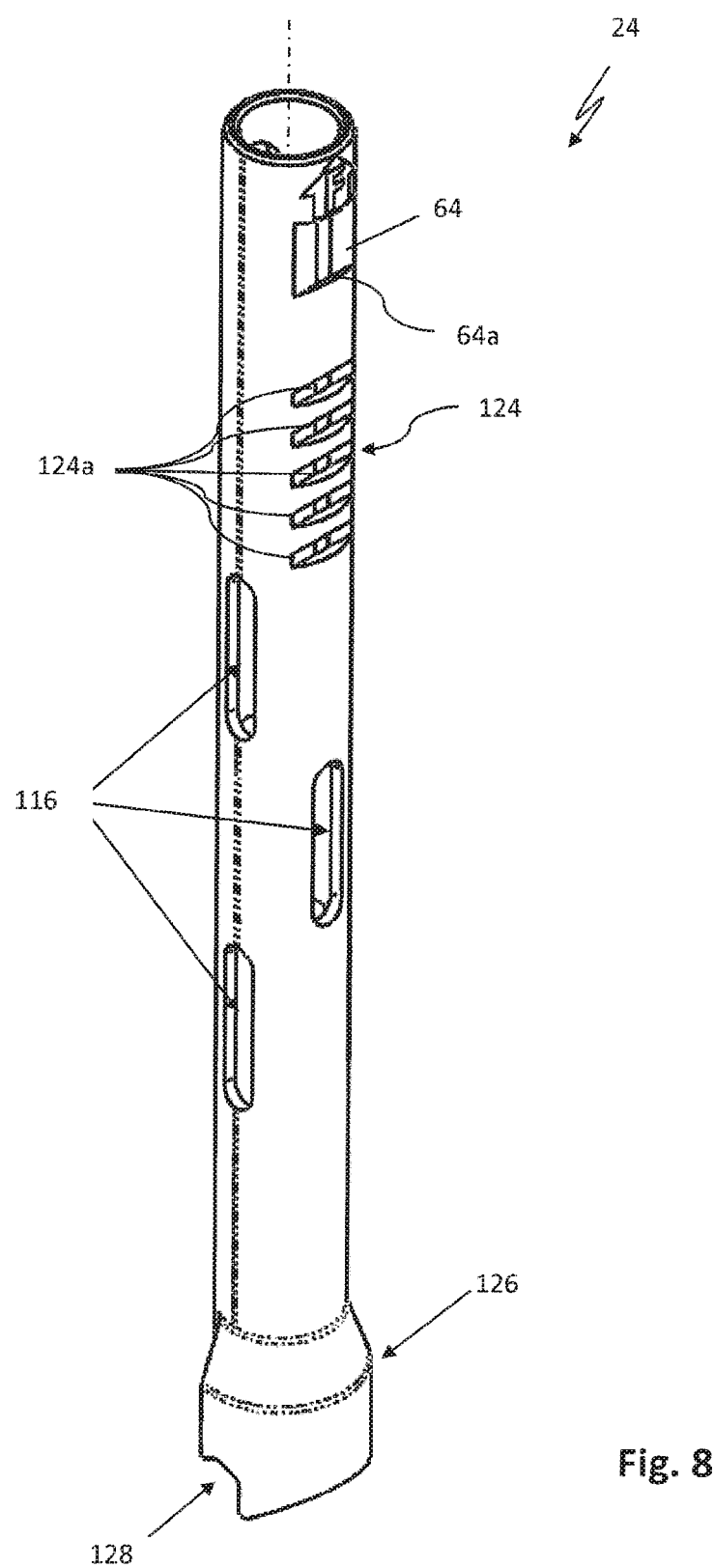
FIG. 8 shows a hollow profile rod presser of the repositioning instrument according to FIG. 1 in a cut away perspective view.

According to the longitudinal views of the repositioning instrument shown in FIGS. 3 and 4 of the repositioning instrument 10 from FIG. 1 and according to the cut away drawings in FIGS. 7 and 8, the locking sleeve 22 and the coupling sleeve 14 each have a lateral wall opening 58. The two wall openings 58 are arranged in the operational state of the repositioning instrument 10 in the radial direction at least partially aligned with each other. The fork-shaped load arm 48 of the actuating lever 40 is coupled to a carrier slide 60. The carrier slide 60 is longitudinally displaceably guided in a T-shaped longitudinal groove 62 in the side wall element 50 in interlocking sliding play.

The carrier slide 60 extends inwardly from the outside in the radial direction through the two lateral wall openings 58 of the locking sleeve 22 and the coupling sleeve 14 and engages in a drive profile 64 of the rod presser 24. The carrier slide is thereby coupled positively or frictionally with the rod presser 14 in the feed direction A of the rod presser 14.

The grip part 26 further has a latching device 66 for the rod presser 24 as well as for the locking sleeve 22. The latching device 66 comprises a receiving compartment 68 arranged in the handle part 26 with a side wall opening 70 and a latching element 72 arranged in the receiving compartment 68. The latching element 72 has a passage opening 74, through which the locking sleeve 22, the coupling sleeve 14 and the rod presser 24 extend with radial play. The latching element 72 is thus formed annularly and surrounds the locking sleeve 22, the coupling sleeve 14 and the rod presser 24 on the outside. As a result, the latching element 72 is secured in the receiving compartment 68 at the same time against unwanted falling out. The latching element 72 is arranged with respect to the longitudinal axis 12 of the repositioning instrument 10 in the receiving compartment with only a slight axial play. A spring element 76 serves to preload the latching element 72 outward in the direction of its movement axis 78, i.e. in the direction of the side wall opening 70. In the release position of the locking sleeve 22 shown, the latching element 72 is preloaded and bears on the inside circumference with a latching edge 80 (FIG. 4) against the locking sleeve 22 on the outside. The latching element 72 is thus here in its inactive state.

The coupling sleeve 14 has, according to FIGS. 3 and 7 in the region of its proximal end portion on two resiliently articulated radial projections 82, which extend in each case in the radial direction outwardly through a slot-shaped recess 84 of the locking sleeve 22 into corresponding bearing recesses 86 of the handle part 26. By means of the radial projections 82, the locking sleeve 22 and the coupling sleeve 14 are rotatably coupled to each other and additionally arranged the coupling sleeve 14 is arranged fixed in position in the axial direction and held about its longitudinal axis 16 on the handle part 26.

Figure 5:
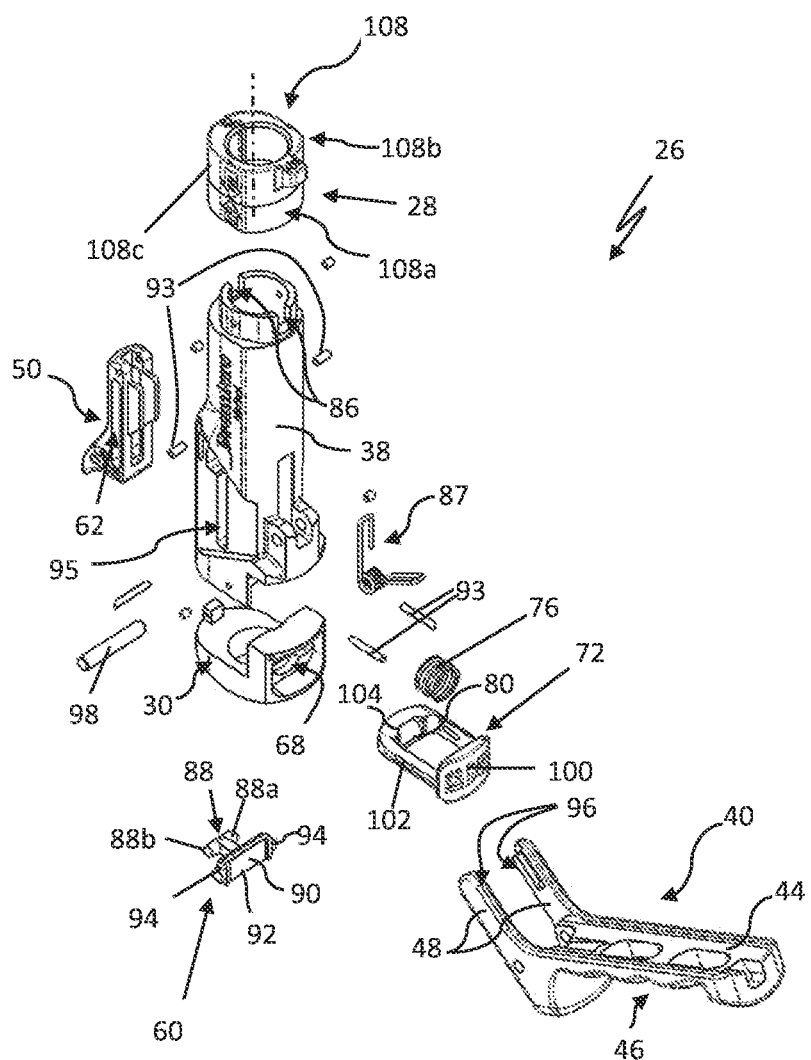
FIG. 5 shows the handle part of the repositioning instrument of FIG. 1 with an exploded representation of its parts, in a perspective view.

In FIG. 5, the handle part 26 of the repositioning instrument 10 is shown in a cut away view and with an exploded view of its parts.

The foot portion 30 of the handle part 26 may be designed as a separate component from the main body 38 of the handle part 26, and may be, in particular, made of metal. The foot section 30 here has the receiving compartment for the rest element 72. The foot portion 30 may be permanently attached to the main body 38 of the handle portion 26 by pins or the like. Other types of attachment are of course conceivable.

The actuating lever 40 can be deflected from its rest position shown in FIGS. 1 to 3 against the force of a preferably two-armed (torsion) spring element 87.

The carrier slide 60 is formed here by way of example in a cufflink-like manner. The carrier slide 60 comprises a T-shaped profile extension 88 with two lateral projections 88a, 88b which engage in the operational state of the repositioning instrument 10 in the T-shaped longitudinal groove 62 of the side wall member 50 of the handle part 26. The profile extension 88 thus serves as a sliding block, which is arranged with tensile strength in the radial direction in the longitudinal groove 62 of the side wall element 50. The carriage slide 60 has a contact surface 90, which is designed to be planar here, for radial contact with the driving profile 64 of the rod presser 24. An axial pressure surface of the carrier slide 60 designated with 92 works together with the profile edge 64a of the driving profile 64 of the rod presser 24 (see FIG. 8) in the axial direction. The side wall member 50 may be pivotally mounted, for example by pins 93 on the main body 38 of the handle part 26.

At the carrier slide 60, bearing journals 94 are formed, which laterally extend away from the carrier slide 60. The carrier slide 60 extends in its installed state in the handle portion 26 in mutually opposite lateral guide slots 95 of the handle part 26 into it. These two bearing journals 94 engage in the operational state in corresponding columns or slots 96 of the fork-shaped load arm 48 of the actuating lever 40. An axle piece designated 98 serves for the pivotable mounting of the actuating lever on the main body 38 of the handle part 26.

The latching element 72 comprises a foot plate 100, which is connected via two profile legs 102 with a latching head 104. The latching element 72 thus has a stirrup shape. The locking edge 80 is formed at the latching head 104. The latching element 72 here consists of metal in order to ensure a sufficiently large mechanical load-bearing capacity of the latching element 72. The clear width of the passage opening 74 of the latching element 72 is selected to be greater than an outer diameter (not designated) of the locking sleeve (FIG. 3).

The head portion 28 of the handle part 26 includes an annular bearing collar 108, preferably made of metal. The bearing bracket 108 has an annularly closed first longitudinal section 108a and an openable second longitudinal section 108b. The first longitudinal section 108a partially comprises the bearing recesses 86 for the radial projections 82 of the coupling sleeve 14 (FIG. 3). The second longitudinal section 108b here has, by way of example, a pivotally hinged closure bar 108c. The closure bar 108c serves to close the proximally open bearing recesses 84 of the handle part 26. As a result, the coupling sleeve 14 and the locking sleeve 22 (FIG. 3) in the grip part 26 can be secured even better against unintentional axial movement of these components from out of the handle part 26.

Figure 6:
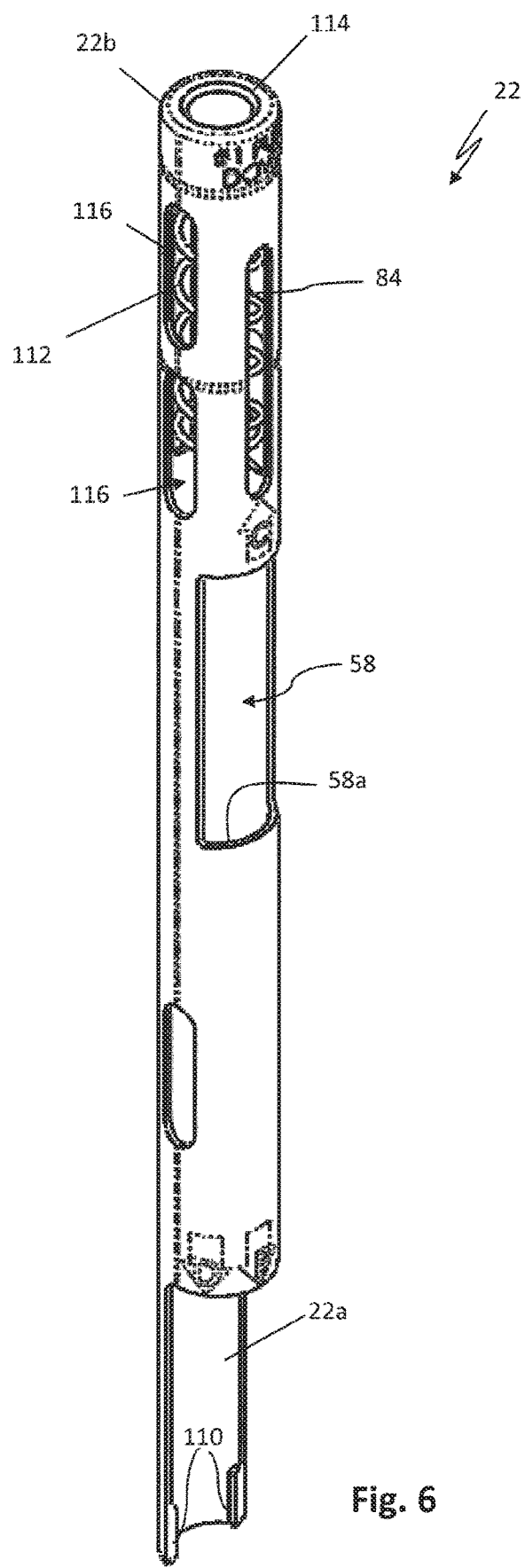
FIG. 6 shows a locking sleeve of the repositioning instrument according to FIG. 1 in a cut away perspective view.

In FIG. 6, the locking sleeve 22 of the repositioning instrument is shown in a cut away view. The wall opening 58 for the carrier slide 72 of the actuating lever 40 (FIG. 5) can be clearly seen. A lower edge of the wall opening 58 is designated 58a. The locking sleeve 22 is supported in its locking position with this lower edge 58a on the latching element 72 in the axial direction. In the release position, the locking sleeve 22 can be supported via the lower edge 58 on the carrier slide 60, preferably on its axial pressure surface 92 (FIG. 5), as shown in FIG. 3.

The locking sleeve 22 here has only one locking extension 22a which at its free edge portion has two radially inwardly projecting and mutually facing guide tongues 110. These guide tongues 110 facilitate the assembly of the locking sleeve 22 on the coupling sleeve 14 and serve to prevent slipping of the latching arms 18 of the coupling sleeve 14 radially outward when the locking sleeve 22 is arranged in its locked position.

A spring element 112 is arranged within the locking sleeve 22, supported on an annular collar 114 at the proximal end 22b of the locking sleeve 22 in the axial direction.

Material recesses 116 serve for a simplified cleaning or disinfection of the locking sleeve 22.

FIG. 7 shows the coupling sleeve 14 in a cut away view. The wall opening 58 has a wall opening (FIG. 6) corresponding to or substantially corresponding to the locking sleeve 22 in shape and size. The two flexibly articulated radial projections 82 are arranged on opposite regions of the coupling sleeve 14. The coupling sleeve 14 has, in a manner corresponding to the locking extension 22a of the locking sleeve 22 (FIG. 6), an axial coupling extension 14a with the two latching arms 18 and with a support or guide arm 118 arranged between the two latching arms 18.

The latching arms 18 each have at their free end portion an inwardly projecting coupling or locking member 120 which is provided for engagement in a corresponding recess of the tulip head. The guide arm 118 and the two latching arms 18 are separated from each other by an axial gap 122. The guide arm 118 is rigid in relation to the latching arms 18 and cannot be deflected in the radial operating direction with respect to the longitudinal axis 12 in normal operational use of the repositioning instrument. The guide arm 118 is thus dimensionally stable overall in the radial direction.

FIG. 8 shows the sleeve-shaped rod presser 24 in a cut away view. The driving profile 64 for the carrier slide 60 (FIG. 5) is embodied here as a single outside depression of the rod presser 24. The lower shoulder or profile edge 64a formed thereby serves for the axial contact of the pressure surface 92 of the carrier slide 60 (FIG. 5).

The rod presser 24 also has an outside latching profile 124 for engaging the latching element 72. Due to the interaction of these two components, the rod presser can be fixed in its respective axial position relative to the coupling sleeve 14. The latching profile 124 here comprises individual grooves 124a, which are spaced apart from each other in the axial direction on the outside of the rod presser 24. According to FIG. 9, the grooves 124a may be linear or curved or, if necessary, designed as circumferential annular grooves. It should be noted that the rod presser 24 is smooth on the inside, and is steplessly executed. However, the rod presser 24 can also be corrugated or rippled in the axial direction.

The rod presser 24 has a distal end portion 126 with end depressions 128 for receiving the fixing rod. The distal end portion may expand in the axial direction. The material recesses 116 of the rod presser 24 essentially serve to reduce weight and simplify hygienic preparation, i.e. cleaning and disinfection or sterilization, of the repositioning instrument.

Figure 9:
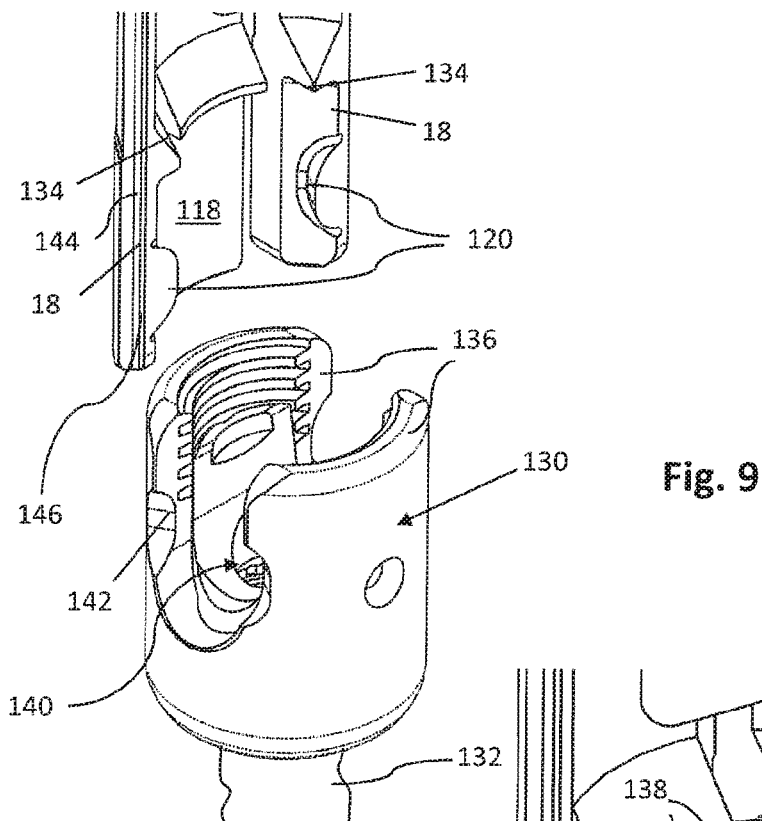
FIG. 9 shows a detail view of the repositioning instrument according to FIG. 1 with a tulip head of a bone screw, in a perspective view.

FIG. 9 shows an enlarged detail of the distal end section of the coupling sleeve 14 during the coupling to the tulip head 130 of a bone screw 132 shown only partially. The latching arms 18 and the guide arm 118 each have an axial stop 134 for a wall leg 136 of the tulip head 130 in order to limit a maximum axial insertion depth of the tulip head 130 between the latching arms 18. The two wall legs 136 of the tulip head 130 are provided in a manner known per se with an internal thread 138, into which a fixing screw (not shown) for permanent fixing of the fixing rod (not shown) in the tulip head 130 can be screwed. A fixing rod connector in the tulip head is designated with 140 and recesses corresponding to the locking members 120 of the coupling sleeve 14 are designated 142.

It should be noted that the latching arms 18 of the coupling sleeve 14 are each provided on their side edge 144 facing away from the guide arm side with a longitudinal groove 146. The longitudinal grooves 144 continue to the proximal end of the coupling sleeve 14 and serve to guide or receive the guide tongues 110 (FIG. 6) of the locking sleeve 22 during assembly as well as during the operational use of the repositioning instrument 10.

Figure 10:
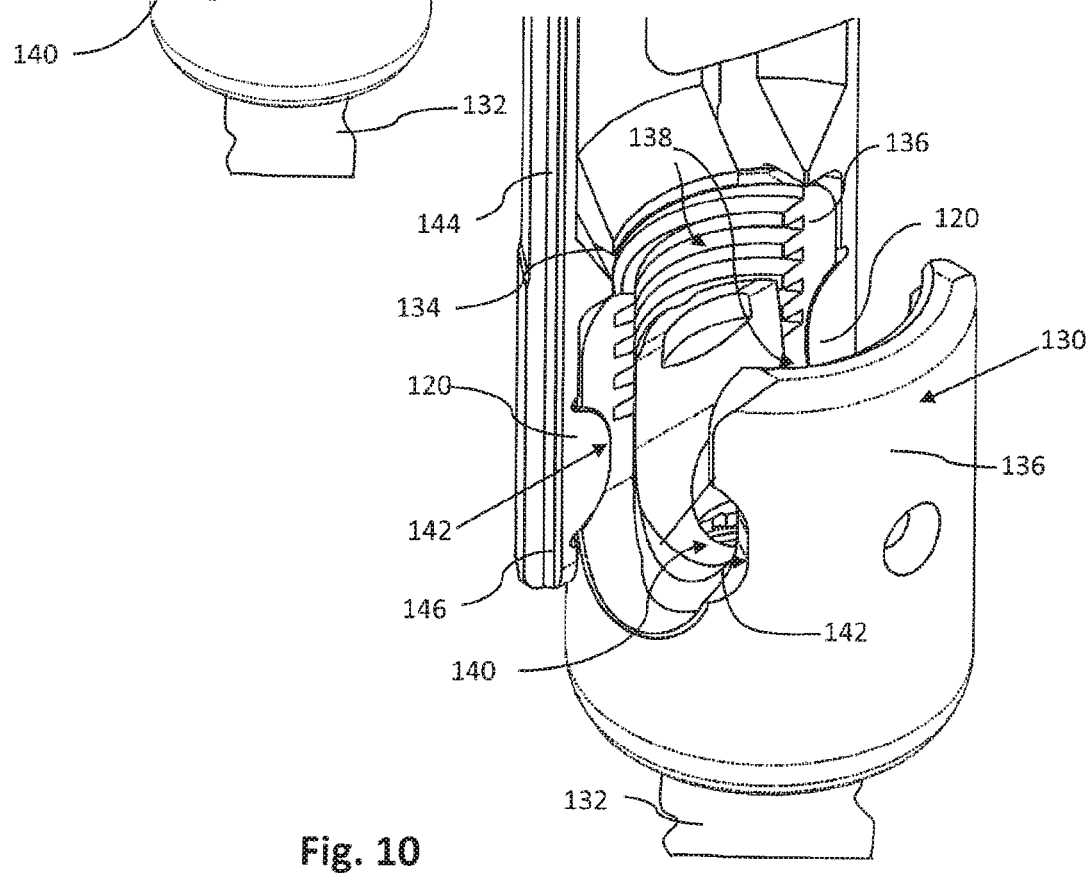
FIG. 10 shows a detailed view of the repositioning instrument according to FIG. 1, which is coupled and locked on the tulip head of a bone screw, in a perspective view.
Figure 11:
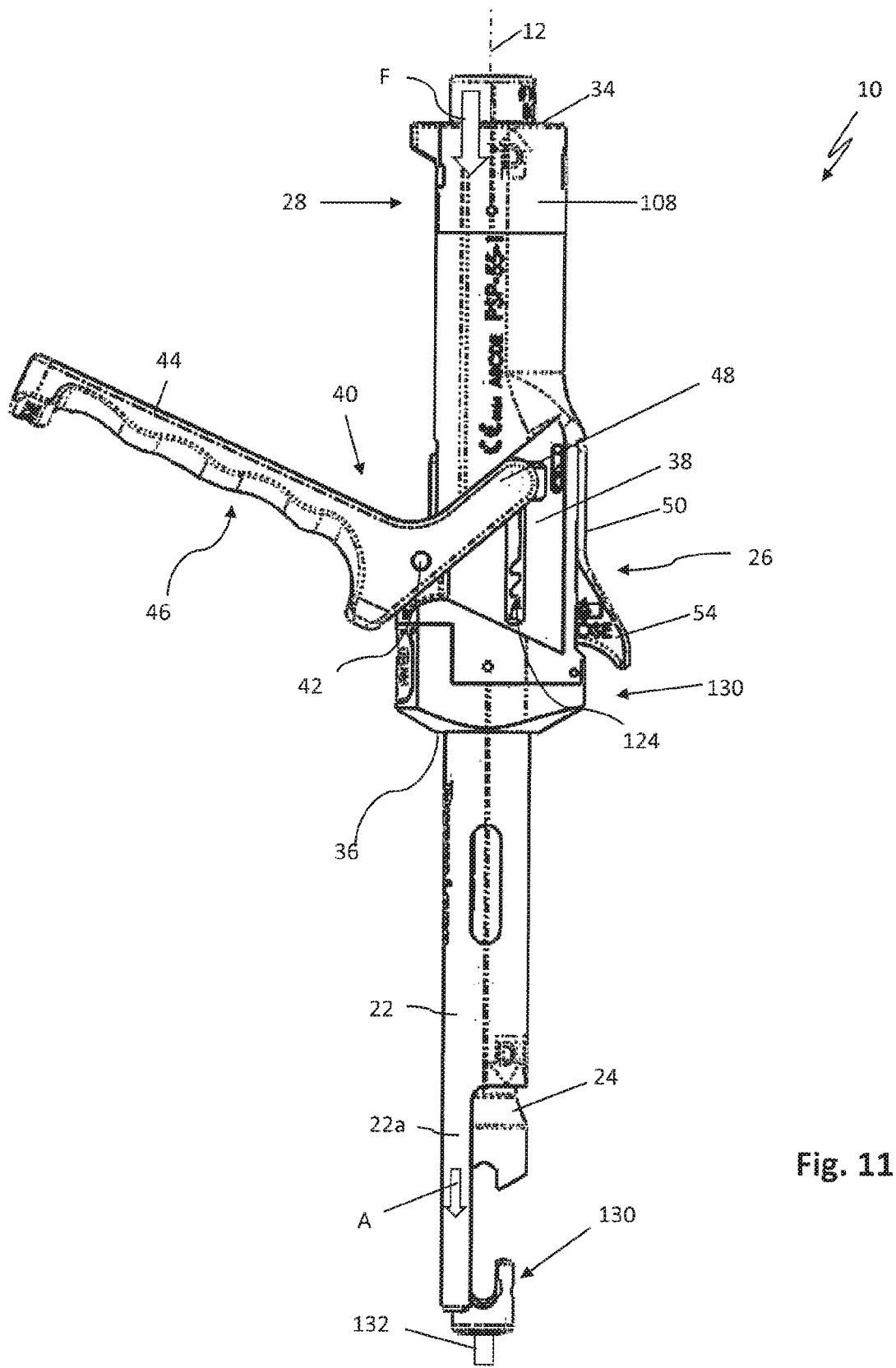
FIG. 11 shows the repositioning instrument according to FIG. 1 in the coupled and locked state on a tulip head, before the rod presser is pressed down.

To couple the repositioning instrument 10 to the tulip head, the coupling sleeve 14 is pushed onto the tulip head 130 in the axial direction. The latching arms 18 are each deflected radially outward by their contact with one of the wall legs 136 of the tulip head 130 until the wall leg 136 strikes against the axial stops 134 and the latching members 120 of the latching arms 18 engage in the radial direction into the corresponding outer recesses 142 of the tulip head 130, as illustrated in FIG. 10.

The coupling sleeve 14 is subsequently secured according to the illustrations in FIGS. 11 to 14 by solely displacing the locking sleeve 22 into its locking position on the tulip head 130 of the bone screw 132. For this purpose, the locking sleeve 22 is manually moved by direct loading of its proximal end 22b with an axially directed force F shown in FIG. 11 into its locking position. In other words, the locking sleeve 22 is displaced distally into its locking position by direct pressure of a finger or several fingers placed on the locking sleeve 22 or the user's hand. This allows a particularly ergonomic, sensitive, controlled and handy operation of the repositioning instrument 10.

Figure 12:
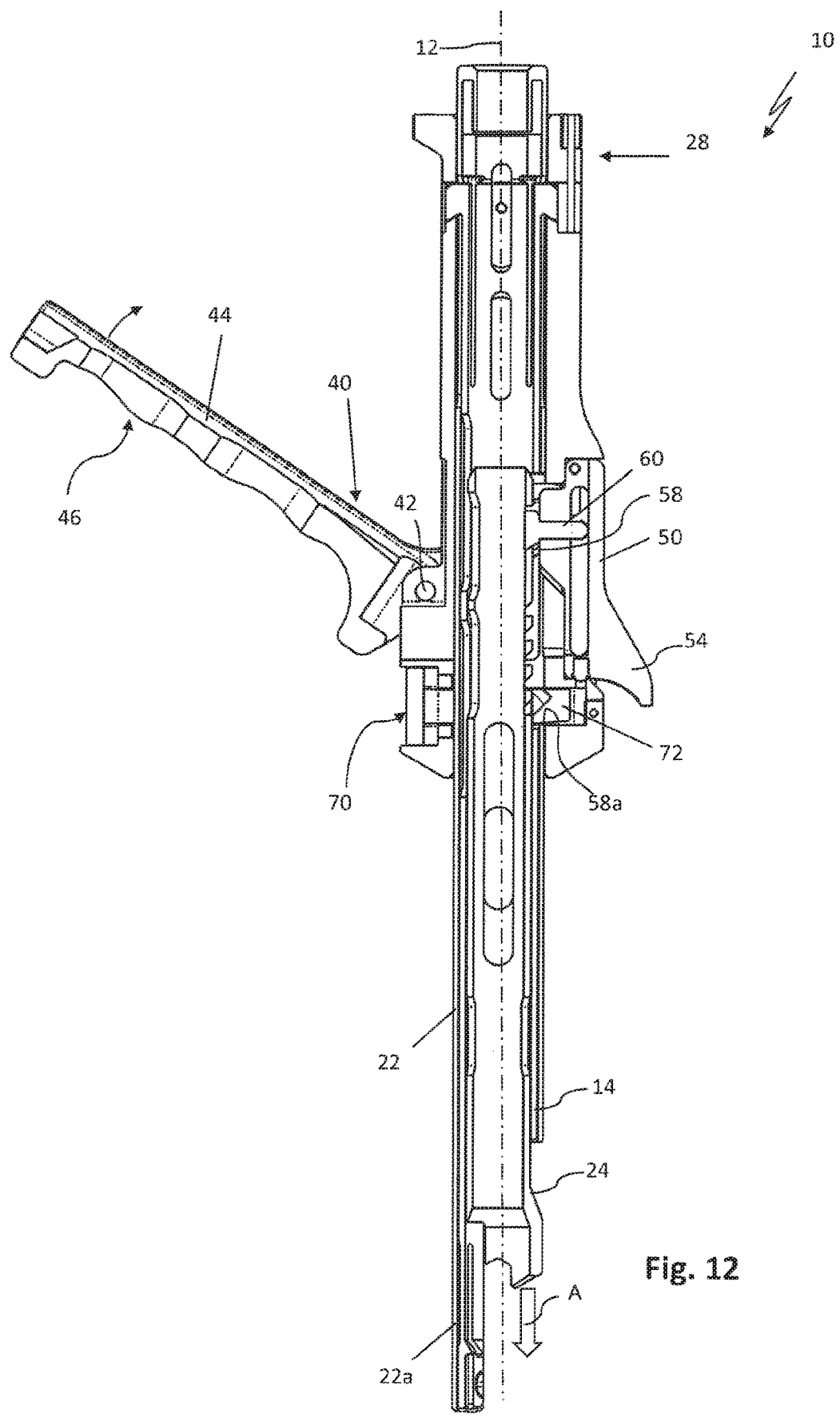
FIG. 12 shows the repositioning instrument according to FIG. 11 in a cut away longitudinal section.

According to FIG. 12, the locking extension 22a of the locking sleeve 22, which is arranged in the locking position, covers the coupling extension 14a of the coupling sleeve 14 in a direction radial to the longitudinal axis 12. A radial deflection of the latching arms 18 latched on the tulip head and a concomitant unwanted disconnection of the coupling sleeve 14 from the tulip head 130 is thereby reliably prevented. The fact that the locking extension 14a of the locking sleeve 22, additionally overlaps the two latching arms 18 in the region of the outer side edges 144 (see FIGS. 9 and 10) and engages in their respective longitudinal groove 146, means that a slipping of the latching arms 18 can be counteracted by the tulip head 130 even under load or an onset of torque.

Figure 13:
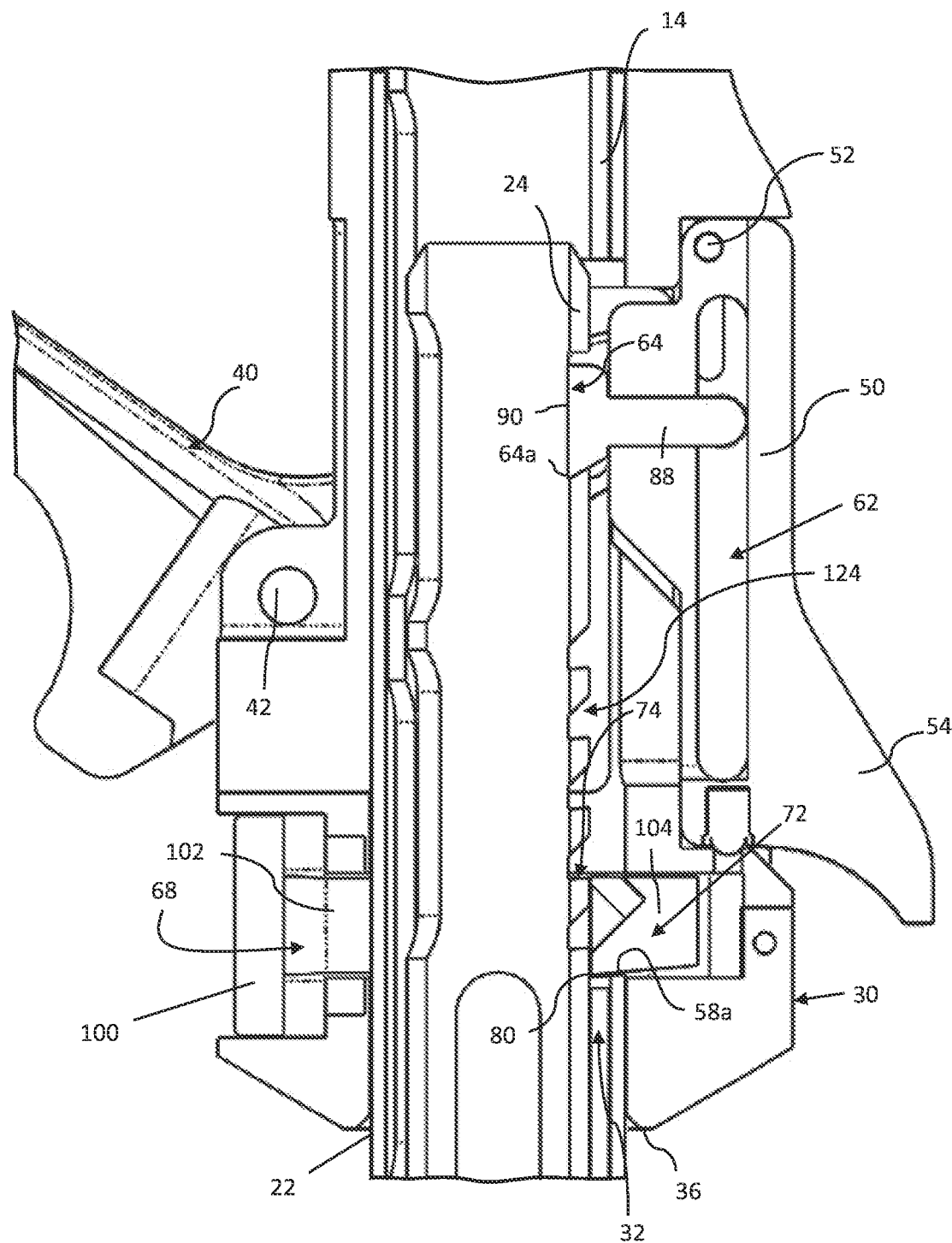
FIG. 13 shows the repositioning instrument according to FIG. 12 in a partial detail enlargement.

In the locking position of the locking sleeve 22, the lateral wall opening 58 of the locking sleeve 22 is arranged in alignment with the latching element in the radial direction. The latching element 72 is moved by the force of the spring element 76 in the radial direction in the locking sleeve 22 until it rests directly outside on the locking edge 80 on the rod presser 24. As a result, the latching element 72 is activated or focused in its latching function with respect to the rod presser 24, as shown in FIG. 13.

It should be noted that the latching element 72 has a double function here. The latching element 72 is, as shown in FIGS. 12 and 13, at the distal edge 58a of the wall opening 58 of the locking sleeve 22 in the axial direction. As a result, an unintentional axial pushing back of the locking sleeve 22 is reliably blocked from its locking position in the direction of its rest position. The repositioning instrument 10 is therefore secured in its position coupled to the head housing 130.

Figure 14:
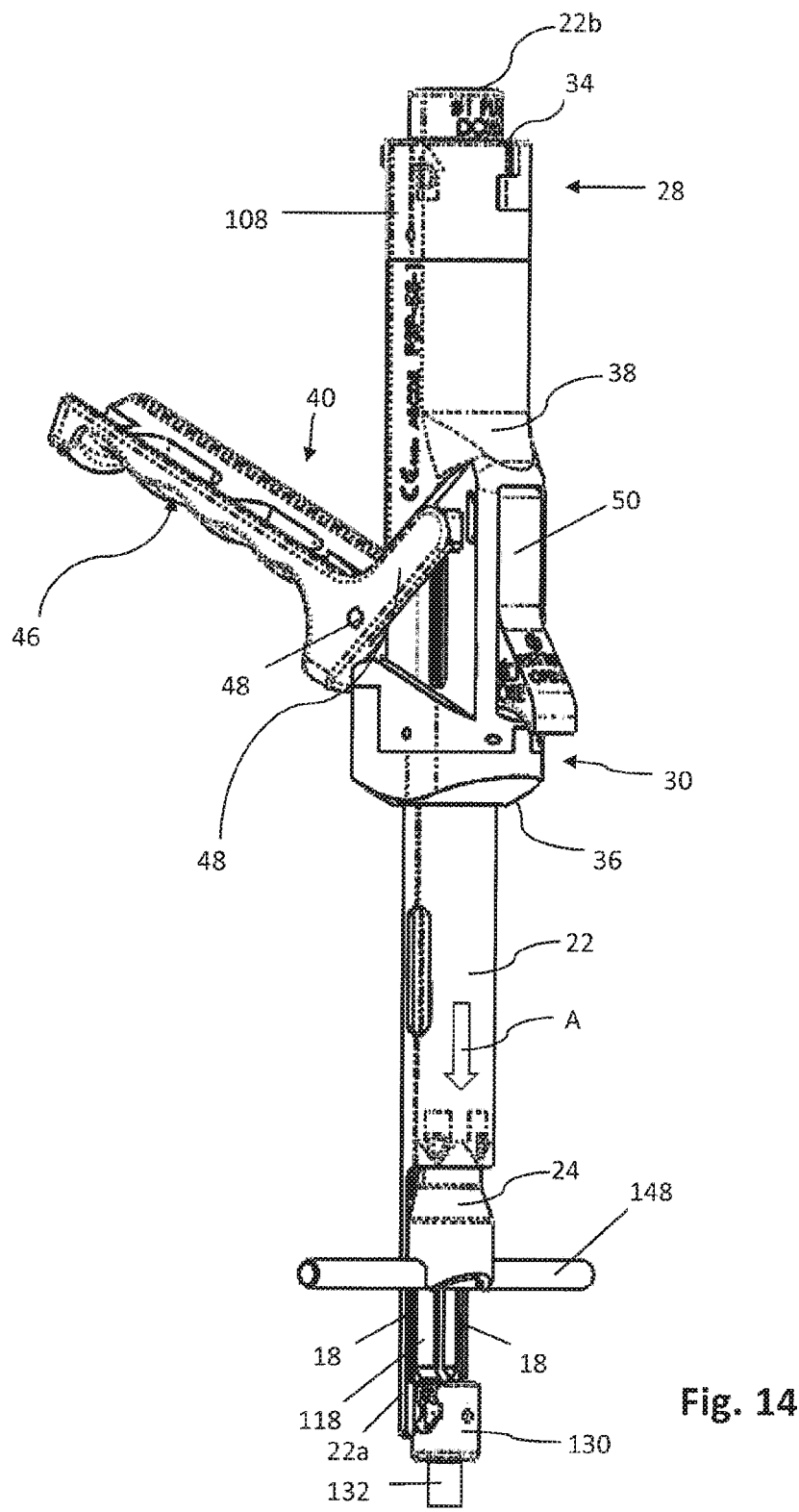
FIG. 14 shows the repositioning instrument according to FIG. 11 with a fixing rod to be lowered into the tulip housing, in a perspective view.
Figure 15:
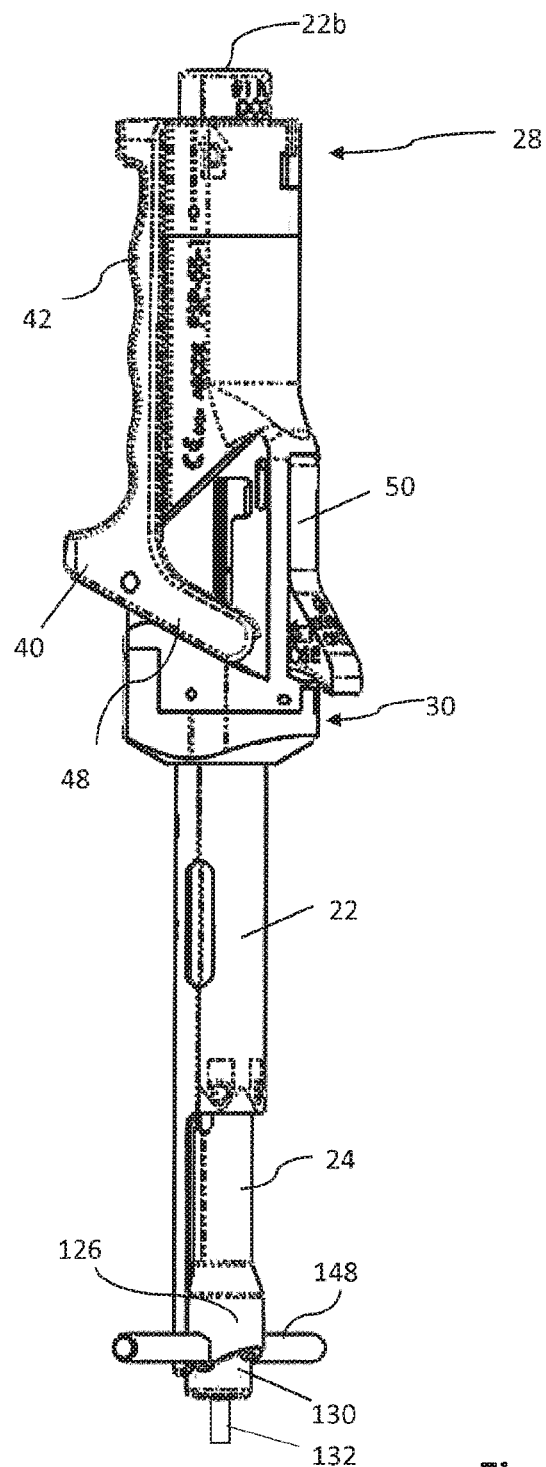
FIG. 15 shows the repositioning instrument according to FIG. 11 after pressing down the rod presser, in a perspective view.
Figure 16:
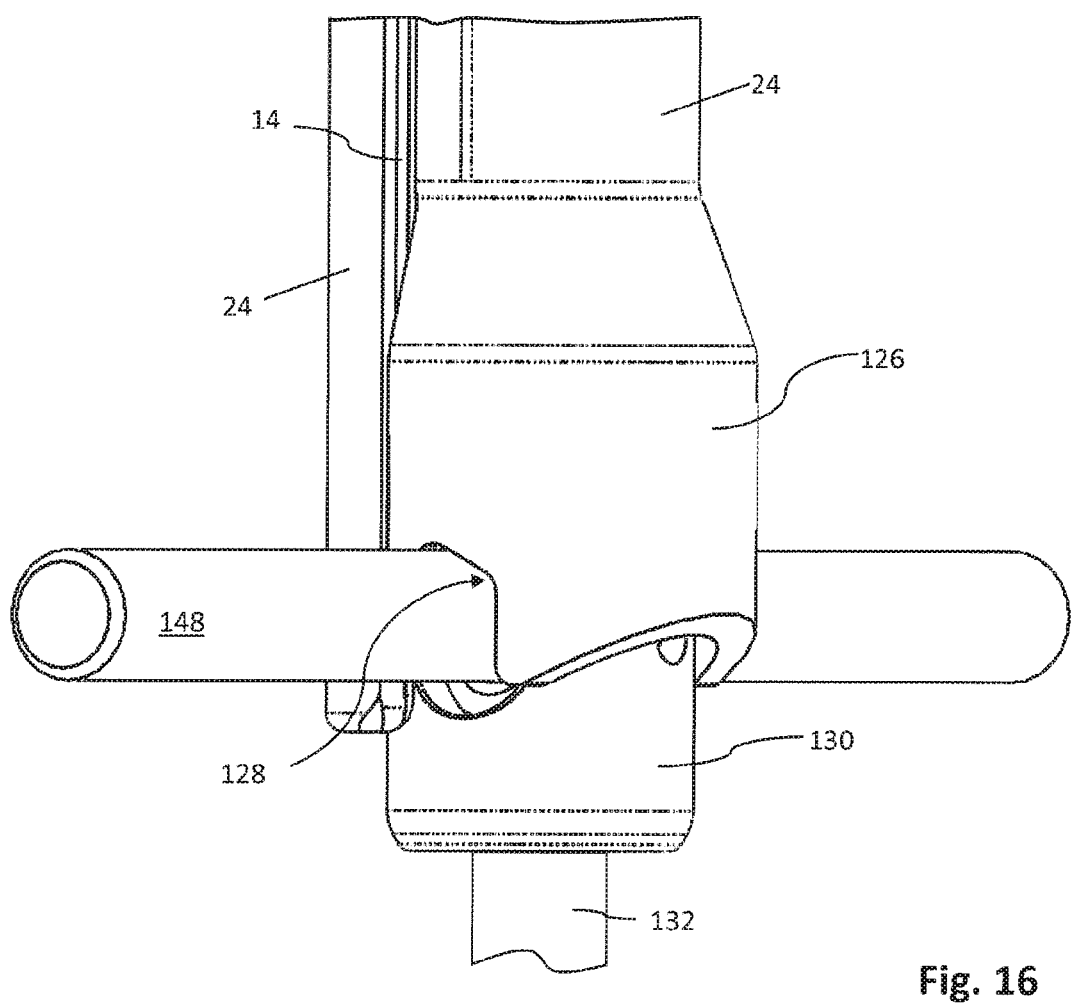
FIG. 16 shows a partial enlarged detail view of the repositioning instrument coupled and locked on the tulip head according to FIG. 11, with a fixing rod completely lowered in the tulip housing, in a perspective illustration.
Figure 17:
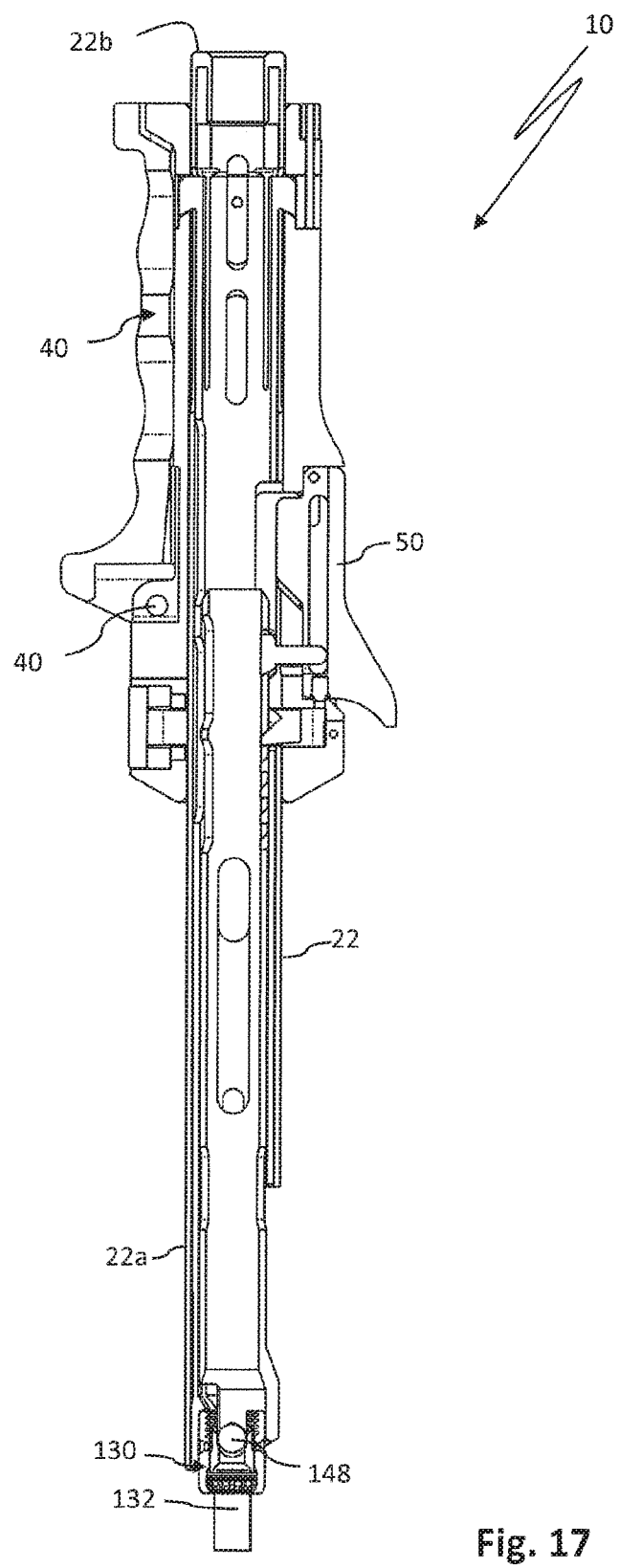
FIG. 17 shows the repositioning instrument according to FIG. 15 in a longitudinal section.
Figure 18:
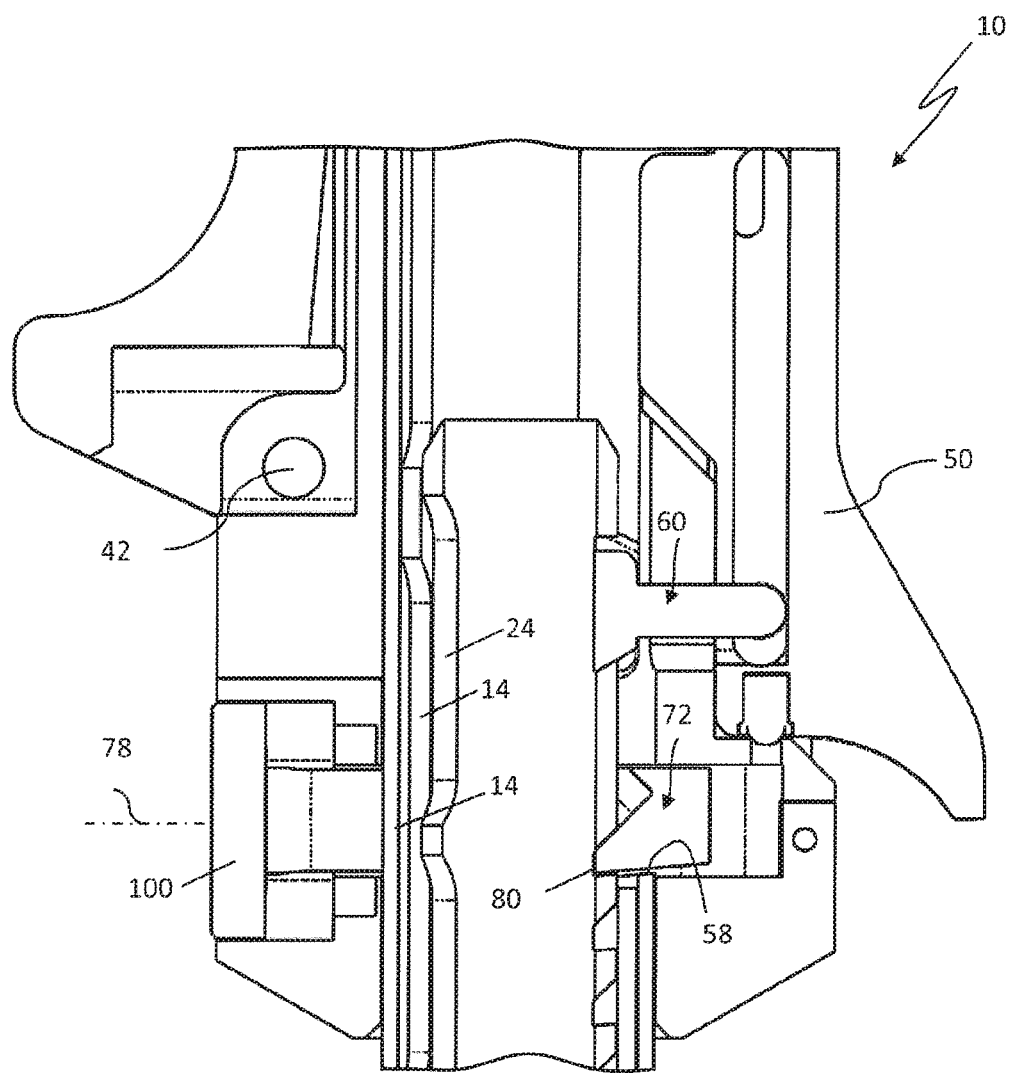
FIG. 18 shows a partial detail enlargement of the repositioning instrument according to FIG. 17.

The fixing rod 148 can now be threaded as shown in FIG. 14 by the user between the rod presser 24 and the head housing 130 of the bone screw and then lowered in the head housing 130 in its predetermined end position with the rod presser 24. This is done by means of the actuating lever 40, which can be easily operated with the hand of the user holding the handle. When the force arm 44 of the actuating lever 40 is pivoted to the handle part 26, the carrier slide 60 and thus the rod presser 24 are moved in the feed direction A.

In the FIGS. 15 to 18, the fixing rod 148 is completely lowered into the fixing rod connector 140 (FIG. 10) of the tulip head 130. The optionally extended distal end portion 126 of the rod presser can engage over one of the wall legs 126 of the tulip head 130 in the radial direction. The tulip head 130 is thereby arranged held in the radial direction between the locking extension 22a and the coupling extension 14b of the repositioning instrument 10. For fixing the fixing rod 140, a fixing screw (not shown) is inserted in a manner known per se, which is inserted through the sleeve-like rod presser 24 into the tulip head 130 and screwed to its wall legs 136 by means of a rotary tool insertable into the rod presser, for example a screwdriver.

For renewed release of the repositioning instrument 10 from the tulip head, the latching element 72 is pushed manually in the radial direction, i.e. along the movement axis 78 of the latching element 70 (FIG. 4), further into the receiving compartment 68 of the handle part 26. The latching element 72 is thereby disengaged in the radial direction from the locking sleeve 22 and from the locking profile 124 of the rod presser 24. The locking sleeve 22 snaps back proximally into its rest position (FIG. 1) in the axial direction by the force of the spring element 112 (FIG. 6).

The rod presser 24 slides back by the force of the (torsion) spring element 87 (FIG. 5) into its initial position shown in FIG. 1 in the axial direction to proximal. The repositioning instrument 10 is now available for renewed operational use.

Figure 19:
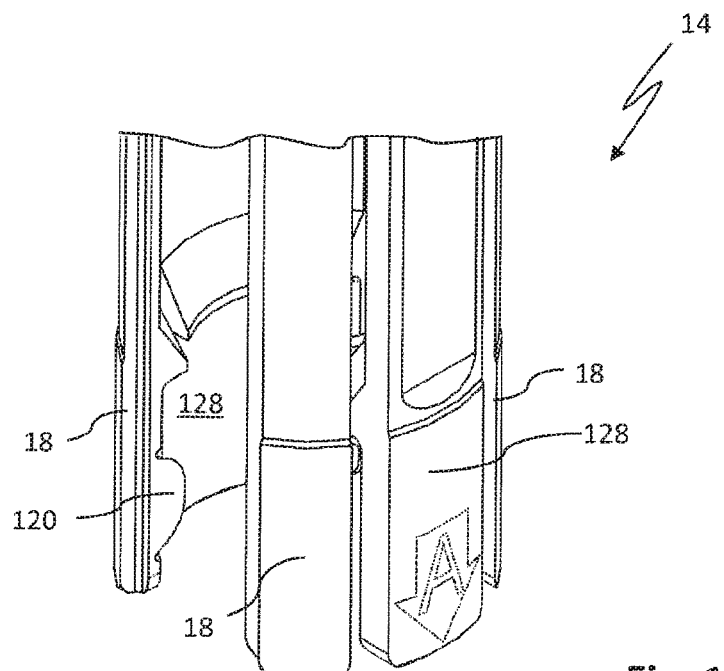
FIG. 19 shows an alternative embodiment of a coupling sleeve of the repositioning instrument according to FIG. 1, in a perspective view.
Figure 20:
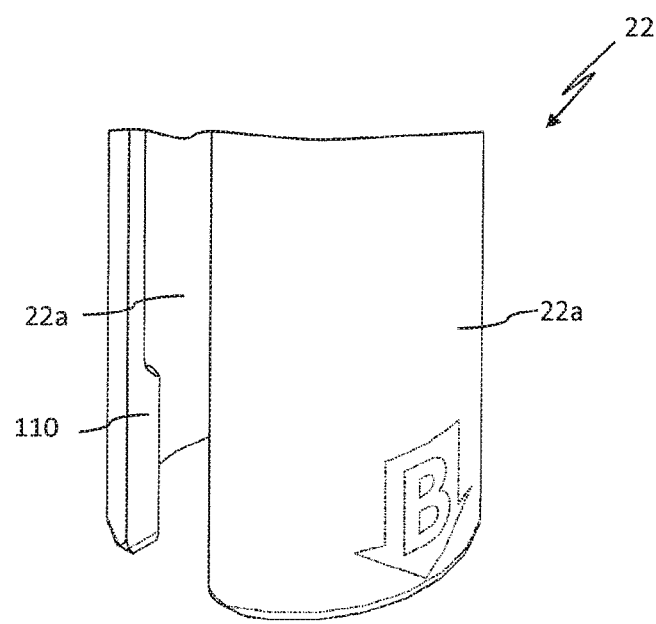
FIG. 20 shows an alternative embodiment of a locking sleeve of the repositioning instrument according to FIG. 1 for a coupling sleeve according to FIG. 19, in a perspective illustration.

The repositioning instrument 10 may, according to an alternative embodiment, also have a coupling sleeve 14 with a total of four latching arms 18 and two guide arms 118, as shown in FIG. 19. The latching arms 18 are arranged here in pairs, each with a guide arm 118 arranged between them, on the coupling sleeve 14. If the coupling sleeve 14 is coupled to the tulip housing 130 of a bone screw 132, the coupling sleeve 14 in this embodiment surrounds both wall legs 136 of the tulip housing 130 on the outside. In this design of the repositioning instrument according to FIG. 20, the locking sleeve 22 has two locking extensions 22a, which are arranged opposite to each other on the coupling sleeve 22 in the radial direction.

Figure 21:
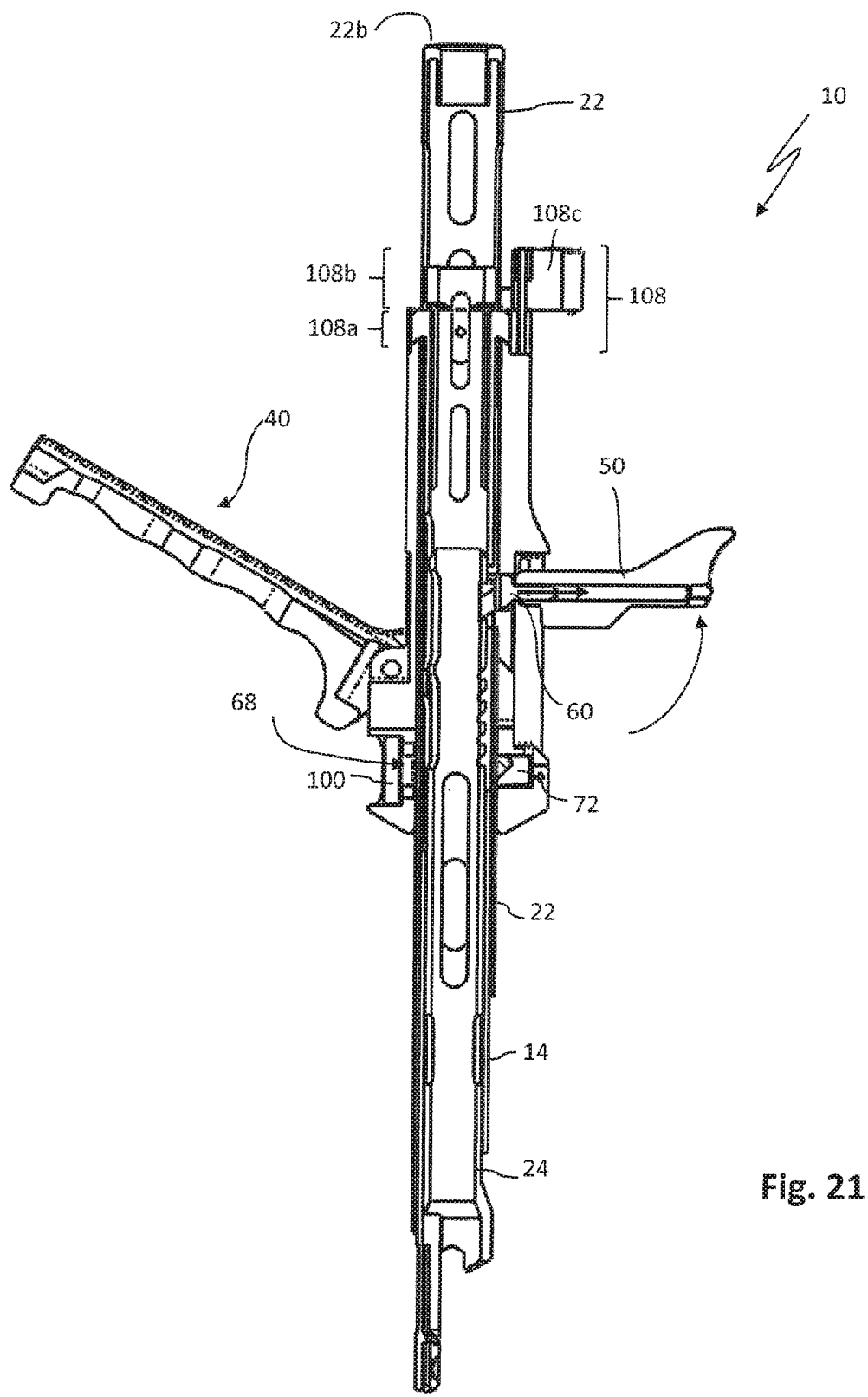
FIG. 21 shows the repositioning instrument of FIG. 1 in the unlocked state for disassembling of the repositioning instrument for the purpose of treatment, in a section view.

To disassemble the repositioning instrument 10, the side wall section 50 is swung out of the handle part 26 in the radial direction, as shown in FIG. 21. As a result, the carrier slide 60 is moved out of the drive profile 64 of the rod presser 24 in the radial direction. The rod presser 24 can now be pulled out of the coupling sleeve 14 in the axial direction to distal, i.e. downward. After opening the bearing bracket 108 and a radially directed pressing in of the two radial projections 82 (FIG. 3) of the coupling sleeve 14, the locking sleeve 22 and the coupling sleeve 14 can be pulled together from the handle part 26 in the proximal direction, i.e. upwards.

Figure 22:
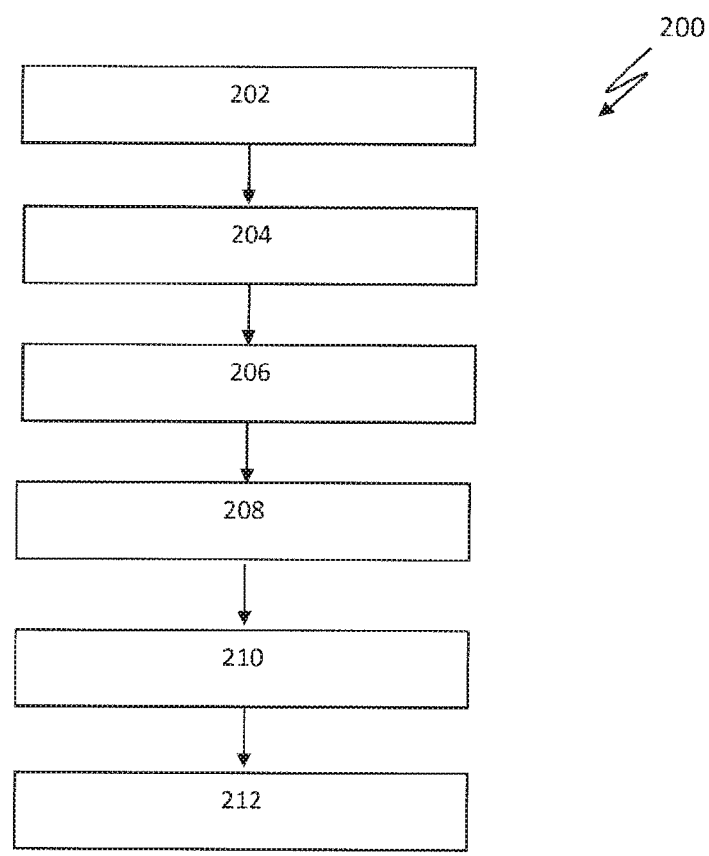
FIG. 22 shows a block diagram of a method according to the invention for mounting the repositioning instrument according to FIG. 1.
Figures 23A, 23B:
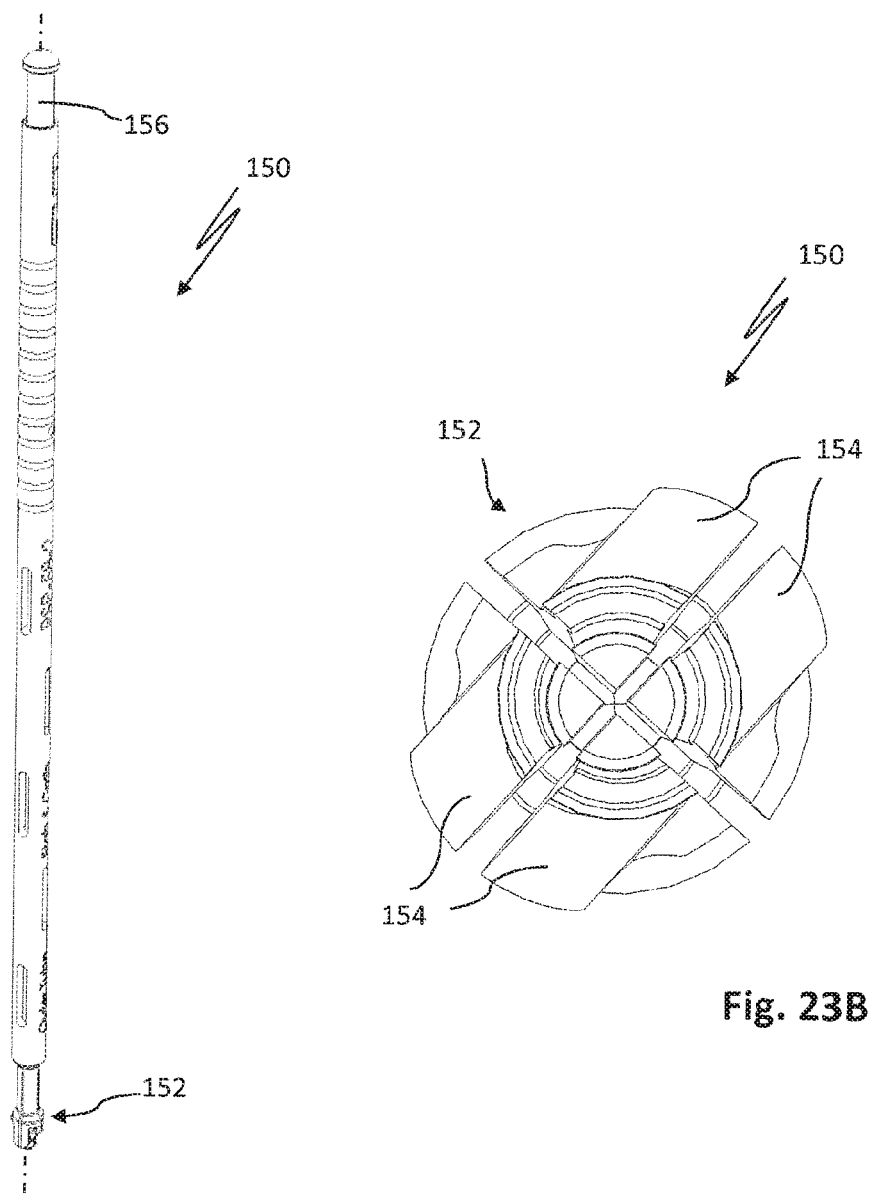
FIG. 23A shows a guide rod for a repositioning instrument according to FIG. 1, which can be mechanically coupled via a coupling section with the tulip head of a bone screw.
FIG. 23B shows the coupling portion of the guide rod in a frontal view.

The assembly method 200 of the repositioning instrument 10 according to the invention is explained below with additional reference to FIG. 22:

In a first step 202, the preassembled handle part 26 and the locking sleeve 22, the coupling sleeve 14 and the rod presser 24 are provided.

In a second step 204, the locking sleeve 22 is pushed in the axial direction from proximal to the coupling sleeve 14, so that the guide tongues 110 of the locking sleeve 22 engage in the corresponding longitudinal grooves 146 of the coupling sleeve 14. The locking sleeve 22 is pushed onto the coupling sleeve 14 until the radial projections 82 of the coupling sleeve 14 each engage in the associated slot-shaped recesses 84 of the locking sleeve 22 and snap in.

In a further step 206, the locking sleeve 22 and the coupling sleeve 14 are inserted together in the axial direction from proximal into the through bore 32 of the handle part 26 with the bearing bracket 108 open until the radial projections 82 of the coupling sleeve 14 in the radial direction engage or snap in into the bearing recesses 86 of the handle part or the bearing bracket 108.

In a subsequent step 208, the bearing bracket 108 is closed.

The rod presser is inserted in a further step 210 coming from distally in the axial direction in the coupling sleeve 14 until it is arranged in its rest position (FIG. 1).

In a further step 212, the side wall element 50 is moved from its opening position pivoted away from the handle part 26 into its closed position (FIG. 1), so that the carrier slide 60 engages in the drive profile 64 of the rod presser. The repositioning instrument 10 is now available for its operational use.

The repositioning instrument 10 explained above in connection with FIGS. 1 to 22 may comprise a guide rod 150, with the aid of which the repositioning instrument 10 can be guided in a simplified manner to the tulip head 130 of the bone screw 132 and coupled thereto. The guide rod 150 has at one end a coupling portion 152 which is insertable and fixable in the tulip head (FIG. 14). This can be done for example via a screw connection. Thus, the coupling portion may be provided with an external thread (not shown) which can be screwed into the internal thread 138 of the wall legs 136 of the tulip head 130. In the embodiment shown in FIGS. 22A and 22B, the coupling portion 152 of the guide rod 150 has four coupling means 154 which can be snapped in the tulip head 130. The coupling means 154 may be moved radially inward by pressing the actuating pin 156 mounted on the other end of the guide rod 150, to decouple the guide rod 150 from the tulip head 130 again. If the guide rod 150 is coupled to the tulip head 130, then the repositioning instrument 10 can be threaded onto the guide rod with the rod presser 24 and advanced on the tulip head 130 in the surgical field in an extremely tissue-preserving manner. After locking the coupling sleeve 14 with the tulip head 130, the guide rod 150 is disconnected from the tulip housing 130 and pulled upwardly out of the rod presser 24.

What is claimed is:

1. A surgical repositioning instrument for lowering and fixing a fixing rod in the tulip head of a bone screw, comprising:
    a coupling sleeve having at least two distal latching arms which are resiliently deflectable for coupling the repositioning instrument to the tulip head of the bone screw in a radial direction to a longitudinal axis of the repositioning instrument;
    a locking sleeve which is longitudinally displaceably arranged on the coupling sleeve between a release position and a locking position, wherein the deflection of the latching arms by the locking sleeve is allowed in its release position and is inhibited in its locking position;
    a rod presser for contacting and lowering the fixing rod slidably arranged within the coupling sleeve;
    a handle part having a through bore in which the locking sleeve, the coupling sleeve and the rod presser are arranged; and
    an actuating lever pivotally mounted on the handle part for advancing the rod presser relative to the coupling sleeve, the actuating lever includes a force arm, the force arm can be manually moved from its rest position, wherein, in the rest position the force arm products laterally from the handle to the handle part and with a load arm coupled to the rod presser, wherein, in the release position, a proximal end of the locking sleeve protrudes from the through bore in the axial direction over the handle part and the locking sleeve is displaceable into its locking position independently of the rod presser by acting on its proximal end with an axially directed force.

2. The repositioning instrument according to claim 1, wherein the locking sleeve can be latched in its locking position relative to the coupling sleeve.

3. The repositioning instrument according to claim 1, wherein the load arm of the actuating lever engages over a longitudinally displaceably mounted carrier slide in the handle part on the rod presser.

4. The repositioning instrument according to claim 3, wherein the carrier slide has bearing journals which each engage a respective slot of the actuating lever.

5. The repositioning instrument according to claim 4, wherein the handle part has a side wall element with a T-shaped, longitudinal groove in which the carrier slide is guided.

6. The repositioning instrument according to claim 5, wherein the side wall element is pivotally mounted on the handle part.

7. The repositioning instrument according to claim 3, wherein the locking sleeve and the coupling sleeve each have a lateral wall opening which are arranged in the operative state of the repositioning instrument in the radial direction at least partially aligned with each other, wherein the carrier slide extends through the lateral wall opening of each of the locking sleeve and the coupling sleeve in the radial direction.

8. The repositioning instrument according to claim 1, wherein the actuating lever can be moved out of its rest position against the force of a torsion spring element.

9. The repositioning instrument according to claim 1, wherein the coupling sleeve has two resiliently articulated, radial projections each extending in the radial direction through a slot-shaped recess of the locking sleeve into a bearing recess of the handle part.

10. The repositioning instrument according to claim 1, wherein the handle part has, at one end, an openable bearing bracket, the bearing bracket consists of metal and which has the bearing recesses for the locking sleeve.

11. The repositioning instrument according to claim 1, wherein the rod presser can be latched by a latching device in its respective axial position relative to the coupling sleeve.

12. The repositioning instrument according to claim 11, wherein the latching device comprises a latching element which is in a grip part, displaceably mounted, and which works together with a latching profile of the rod presser.

13. The repositioning instrument according to claim 12, wherein the latching element surrounds the locking sleeve, the coupling sleeve and the rod presser in an annular manner.

14. The repositioning instrument according to claim 12, wherein the latching element is arranged radially biased by the force of a spring element in the direction of its detent position on the rod presser.

15. The repositioning instrument according to claim 14, wherein the locking sleeve can be locked in its locking position relative to the coupling sleeve by the latching element.

16. The repositioning instrument according to claim 7, wherein a latching element in a locking position of the locking sleeve extends in sections over the lateral wall opening of the locking sleeve in the radial direction into the locking sleeve and abuts in the axial direction a lower edge of the lateral wall opening of the coupling sleeve.

17. The repositioning instrument according to claim 1, wherein the coupling sleeve has a distal free end portion, the distal free end portion has a guide arm which extends in the axial direction between two locking tongues and is spaced apart from each of these to form an axial gap, wherein the guide arm is rigid in comparison to the locking tongues, wherein the guide arm is formed dimensionally stably in the radial direction.

18. The repositioning instrument according to claim 1, wherein the coupling sleeve has two further latching arms, between which a stop extends in the axial direction.

19. The repositioning instrument according to claim 1, wherein the locking sleeve at its distal free end portion has guide tongues, each engaging in a corresponding longitudinal groove of the coupling sleeve, wherein the longitudinal grooves each extend at least in sections on a side edge of one of the latching arms.

20. The repositioning instrument according to claim 19, wherein the longitudinal grooves each extend to a proximal end of the coupling sleeve.

21. The repositioning instrument according to claim 1, wherein the locking sleeve can be moved against the force of a spring element, arranged within the locking sleeve, from its release position into the locking position.

* * * * *